(12) United States Patent
Tarkington et al.

(10) Patent No.: US 11,904,204 B2
(45) Date of Patent: Feb. 20, 2024

(54) DEVICES AND METHODS FOR EXERCISING AN ANKLE, FOOT, AND/OR LEG

(71) Applicant: TS MEDICAL LLC, McLean, VA (US)

(72) Inventors: Mary Anne Tarkington, McLean, VA (US); Peter-Christoph Tarkington Schmidt, McLean, VA (US); David G. Matsuura, Solana Beach, CA (US); Jacob A. Moebius, Encinitas, CA (US)

(73) Assignee: TS MEDICAL LLC, McLean, VA (US)

( * ) Notice: Subject to any disclaimer, the term of this patent is extended or adjusted under 35 U.S.C. 154(b) by 213 days.

(21) Appl. No.: 16/975,577

(22) PCT Filed: Jan. 24, 2019

(86) PCT No.: PCT/US2019/015031
§ 371 (c)(1),
(2) Date: Aug. 25, 2020

(87) PCT Pub. No.: WO2019/164633
PCT Pub. Date: Aug. 29, 2019

(65) Prior Publication Data
US 2020/0406093 A1    Dec. 31, 2020

Related U.S. Application Data

(60) Provisional application No. 62/731,514, filed on Sep. 14, 2018, provisional application No. 62/635,165, filed on Feb. 26, 2018.

(51) Int. Cl.
*A63B 23/08*    (2006.01)
*A63B 21/008*   (2006.01)
(Continued)

(52) U.S. Cl.
CPC ............ *A63B 23/08* (2013.01); *A63B 21/008* (2013.01); *A63B 21/00069* (2013.01);
(Continued)

(58) Field of Classification Search
CPC ..... A63B 23/08; A63B 23/10; A63B 21/4013; A63B 21/4015; A63B 21/015;
(Continued)

(56) References Cited

U.S. PATENT DOCUMENTS 1,509,793 A    9/1924  Thompson et al.
2,021,801 A    11/1935 Meyer
(Continued)

FOREIGN PATENT DOCUMENTS

CN    111184601 A  *  5/2020
DE    548527 C        10/1932
(Continued)

OTHER PUBLICATIONS

Office Action in U.S. Appl. No. 13/482,844, dated Aug. 31, 2012.
(Continued)

*Primary Examiner* — Jennifer Robertson
(74) *Attorney, Agent, or Firm* — JONES ROBB, PLLC

(57) ABSTRACT

An exercise device includes a foot support portion pivotably connected to a leg support portion and having a neutral position relative to a pivot axis. The support portion is configured to rotate about the neutral pivot axis in a first direction away from the neutral position and in a second direction away from the neutral position. The second direction is opposite the first direction. The exercise device also includes a resistance mechanism configured to exert a force on the foot support portion about the pivot axis opposite to the respective first and second directions of rotation of the foot support portion about the pivot axis.

27 Claims, 23 Drawing Sheets

(51) Int. Cl.
  *A63B 21/00*   (2006.01)
  *A63B 21/015*  (2006.01)
  *A63B 21/045*  (2006.01)
  *A63B 23/035*  (2006.01)
  *A63B 23/10*   (2006.01)
  *A63B 22/00*   (2006.01)

(52) U.S. Cl.
  CPC .... *A63B 21/0083* (2013.01); *A63B 21/00181* (2013.01); *A63B 21/00845* (2015.10); *A63B 21/015* (2013.01); *A63B 21/045* (2013.01); *A63B 21/4013* (2015.10); *A63B 21/4015* (2015.10); *A63B 21/4034* (2015.10); *A63B 21/4049* (2015.10); *A63B 23/03508* (2013.01); *A63B 23/10* (2013.01); *A63B 2022/0097* (2013.01); *A63B 2209/10* (2013.01); *A63B 2210/50* (2013.01); *A63B 2213/00* (2013.01); *A63B 2213/004* (2013.01); *A63B 2220/17* (2013.01); *A63B 2225/20* (2013.01); *A63B 2225/50* (2013.01); *A63B 2225/62* (2013.01); *A63B 2225/64* (2013.01); *A63B 2225/66* (2013.01); *A63B 2230/04* (2013.01); *A63B 2230/10* (2013.01); *A63B 2230/50* (2013.01); *A63B 2230/60* (2013.01)

(58) Field of Classification Search
  CPC ... A63B 21/00181; A61F 5/0111–0113; A61H 9/0078
  See application file for complete search history.

(56) References Cited

U.S. PATENT DOCUMENTS

| | | |
|---|---|---|
| 2,268,747 A | 1/1942 | Gaugler |
| 3,259,385 A | 7/1966 | Boren |
| 3,286,709 A | 11/1966 | Hoyer et al. |
| 3,318,304 A | 5/1967 | Vladimir et al. |
| 3,421,760 A | 1/1969 | Freeman et al. |
| 3,511,500 A | 5/1970 | Dunn |
| 3,525,522 A | 8/1970 | Piller |
| 3,741,540 A | 6/1973 | Shimizu |
| 4,111,416 A | 9/1978 | Jinotti |
| 4,199,137 A | 4/1980 | Giguere |
| 4,306,714 A | 12/1981 | Loomis et al. |
| 4,337,939 A | 7/1982 | Hoyle et al. |
| 4,370,977 A | 2/1983 | Mauldin et al. |
| 4,422,635 A | 12/1983 | Herod et al. |
| 4,429,868 A | 2/1984 | LeBlanc et al. |
| 4,501,421 A | 2/1985 | Kane et al. |
| 4,574,785 A | 3/1986 | Yamamoto |
| 4,605,220 A | 8/1986 | Troxel |
| 4,637,379 A | 1/1987 | Saringer |
| 4,669,722 A | 6/1987 | Rangaswamy |
| 4,694,684 A | 9/1987 | Campbell, III |
| 4,718,665 A | 1/1988 | Airy et al. |
| 4,733,859 A | 3/1988 | Kock et al. |
| 4,739,986 A | 4/1988 | Kucharik et al. |
| 4,779,866 A * | 10/1988 | Marshall .......... A63B 21/00069 482/116 |
| D299,063 S | 12/1988 | Young et al. |
| 4,795,148 A | 1/1989 | Rangaswamy |
| 4,801,138 A | 1/1989 | Airy et al. |
| 4,816,920 A | 3/1989 | Paulsen |
| 4,822,039 A | 4/1989 | Gonzalez et al. |
| 4,836,531 A | 6/1989 | Niks |
| 4,979,737 A | 12/1990 | Kock |
| 5,014,690 A | 5/1991 | Hepburn et al. |
| 5,038,758 A | 8/1991 | Iams et al. |
| 5,041,717 A | 8/1991 | Shay, III et al. |
| 5,048,783 A | 9/1991 | Grimes |
| 5,052,379 A | 10/1991 | Airy et al. |
| 5,074,000 A | 12/1991 | Soltani et al. |
| 5,108,092 A | 4/1992 | Hurst |
| 5,129,872 A | 7/1992 | Dalton et al. |
| 5,209,716 A | 5/1993 | Frydman et al. |
| 5,215,508 A * | 6/1993 | Bastow .................. A63B 23/08 482/79 |
| 5,230,681 A | 7/1993 | Hannum et al. |
| 5,263,911 A | 11/1993 | Frydman et al. |
| 5,306,222 A | 4/1994 | Wilkinson |
| 5,337,737 A | 8/1994 | Rubin et al. |
| 5,352,185 A | 10/1994 | Blauth et al. |
| 5,368,536 A | 11/1994 | Stodgell |
| 5,454,769 A | 10/1995 | Chen |
| 5,465,428 A | 11/1995 | Earl |
| 5,489,251 A | 2/1996 | Robles, Jr. |
| 5,520,627 A | 5/1996 | Malewicz |
| 5,570,472 A | 11/1996 | Dicker |
| 5,582,567 A | 12/1996 | Chang |
| 5,606,745 A | 3/1997 | Gray |
| 5,611,770 A | 3/1997 | Tesch |
| 5,645,516 A | 7/1997 | Foster |
| 5,722,919 A | 3/1998 | Timmer |
| 5,727,254 A | 3/1998 | Dicker |
| 5,733,249 A | 3/1998 | Katzin et al. |
| 5,743,837 A | 4/1998 | Dias et al. |
| 5,755,651 A | 5/1998 | Homyonfer et al. |
| 5,788,618 A | 8/1998 | Joutras |
| 5,839,122 A | 11/1998 | Dicker et al. |
| 5,842,959 A | 12/1998 | Wilkinson |
| 5,851,166 A | 12/1998 | Bernardson |
| 5,857,947 A | 1/1999 | Dicker et al. |
| 5,867,826 A | 2/1999 | Wilkinson |
| 5,873,847 A | 2/1999 | Bennett et al. |
| 5,879,276 A | 3/1999 | Miller |
| 5,897,464 A | 4/1999 | Mcleod |
| 6,010,468 A | 1/2000 | Grove et al. |
| 6,024,714 A | 2/2000 | Katzin |
| 6,047,406 A | 4/2000 | Dicker et al. |
| 6,063,013 A | 5/2000 | Vathappallil |
| 6,206,807 B1 | 3/2001 | Cowans et al. |
| 6,217,488 B1 | 4/2001 | Bernardson |
| 6,244,992 B1 | 6/2001 | James |
| 6,254,034 B1 | 7/2001 | Carpenter |
| 6,261,253 B1 | 7/2001 | Katzin |
| D446,264 S | 8/2001 | Fischer et al. |
| 6,277,057 B1 | 8/2001 | Hayden |
| 6,283,897 B1 | 9/2001 | Patton |
| 6,390,957 B1 | 5/2002 | Knight |
| 6,436,058 B1 | 8/2002 | Krahner et al. |
| D469,486 S | 1/2003 | Olson |
| 6,569,213 B1 | 5/2003 | Busch |
| 6,572,514 B1 | 6/2003 | Calafato |
| 6,589,141 B1 | 7/2003 | Flaggs |
| 6,656,097 B2 | 12/2003 | Karecki |
| 6,705,975 B2 | 3/2004 | Kuo |
| 6,780,142 B1 | 8/2004 | Takizawa et al. |
| 6,796,928 B1 | 9/2004 | Christopher et al. |
| 6,808,476 B2 | 10/2004 | Zagone |
| 6,821,235 B1 | 11/2004 | Johnson et al. |
| 6,837,831 B2 | 1/2005 | Lee |
| 7,008,357 B2 | 3/2006 | Winkler |
| 7,074,204 B2 | 7/2006 | Fujii et al. |
| 7,160,231 B2 | 1/2007 | Kazemi |
| D538,814 S | 3/2007 | Cranford et al. |
| D553,379 S | 10/2007 | Genelli |
| 7,294,114 B1 | 11/2007 | Clement et al. |
| 7,316,637 B2 | 1/2008 | German et al. |
| 7,322,904 B2 | 1/2008 | Takizawa et al. |
| 7,364,534 B2 | 4/2008 | Zoller et al. |
| 7,398,571 B2 | 7/2008 | Souke et al. |
| 7,452,340 B2 | 11/2008 | Cook et al. |
| 7,481,739 B2 | 1/2009 | Takizawa et al. |
| 7,481,751 B1 | 1/2009 | Arnold |
| 7,485,074 B2 | 2/2009 | Chen |
| 7,500,324 B1 | 3/2009 | Power et al. |
| 7,537,555 B2 | 5/2009 | Soletski |
| 7,641,591 B2 | 1/2010 | Takizawa et al. |
| D613,409 S | 4/2010 | Genelli |
| 7,771,327 B1 | 8/2010 | Reams |
| 7,775,941 B2 | 8/2010 | Nguyen et al. |
| 7,883,451 B2 | 2/2011 | Hand |

(56) References Cited

U.S. PATENT DOCUMENTS

| | | |
|---|---|---|
| 7,892,154 B1 | 2/2011 | Alexa |
| 7,918,813 B2 | 4/2011 | Drake et al. |
| 8,015,638 B2 | 9/2011 | Shimada et al. |
| 8,029,420 B1 | 10/2011 | Thati |
| 8,092,350 B2 | 1/2012 | Chinag |
| 8,123,663 B2 | 2/2012 | Fey et al. |
| 8,231,508 B1 | 7/2012 | Rousseau |
| 8,246,522 B2 | 8/2012 | Piaget et al. |
| 8,267,839 B1 | 9/2012 | Bartolotta |
| 8,312,566 B2 | 11/2012 | Weir et al. |
| 8,353,854 B2 | 1/2013 | Horst et al. |
| 8,360,940 B2 | 1/2013 | Kole et al. |
| 8,366,591 B2 | 2/2013 | Patoglu |
| 8,403,817 B2 | 3/2013 | Ferguson et al. |
| 8,430,796 B1 | 4/2013 | Tarkington et al. |
| D681,750 S | 5/2013 | Meyer-Hayoz |
| 8,460,163 B2 | 6/2013 | Gibbons |
| 8,480,546 B2 | 7/2013 | Spencer |
| D695,367 S | 12/2013 | Lovegrove et al. |
| 8,678,979 B2 | 3/2014 | Stark et al. |
| D712,044 S | 8/2014 | Mathew et al. |
| 8,827,873 B2 | 9/2014 | Arnstein |
| 8,840,530 B2 | 9/2014 | Baker et al. |
| 8,986,177 B2 | 3/2015 | von Hoffmann et al. |
| D726,844 S | 4/2015 | Mathew et al. |
| D734,411 S | 7/2015 | Powers et al. |
| 9,072,645 B2 | 7/2015 | Gamman et al. |
| 9,095,177 B2 | 8/2015 | Ota et al. |
| 9,114,277 B2 | 8/2015 | Goeckel |
| 9,192,806 B2 | 11/2015 | Mial |
| 9,230,057 B2 | 1/2016 | Stark et al. |
| 9,247,784 B2 | 2/2016 | Stewart |
| 9,295,303 B2 | 3/2016 | Baker et al. |
| D753,777 S | 4/2016 | Radtke |
| 9,302,137 B1 | 4/2016 | Yelvington |
| 9,327,156 B2 | 5/2016 | von Hoffmann et al. |
| 9,377,079 B2 | 6/2016 | DeHarde |
| 9,433,814 B2 | 9/2016 | von Hoffmann et al. |
| 9,474,673 B2 | 10/2016 | Horst et al. |
| D776,211 S | 1/2017 | Gebhard et al. |
| D776,769 S | 1/2017 | Heath |
| 9,539,135 B2 | 1/2017 | Romo et al. |
| 9,566,469 B1 | 2/2017 | Rector |
| 9,592,416 B2 | 3/2017 | Thorpe |
| 9,603,768 B1 | 3/2017 | Widmer et al. |
| 9,656,117 B2 | 5/2017 | von Hoffmann et al. |
| 9,737,753 B2 | 8/2017 | Chuang |
| 9,770,617 B2 | 9/2017 | von Hoffmann et al. |
| 9,814,273 B2 | 11/2017 | Nordstrom et al. |
| D804,590 S | 12/2017 | Hillson |
| D805,590 S | 12/2017 | Heath |
| D806,190 S | 12/2017 | Failing |
| 9,849,328 B1 | 12/2017 | Fulks |
| 9,872,789 B2 | 1/2018 | Sorrenti et al. |
| 9,873,017 B2 | 1/2018 | Barel |
| 9,895,569 B2 | 2/2018 | Yao |
| 9,914,009 B2 | 3/2018 | Tarkington et al. |
| 9,930,928 B2 | 4/2018 | Whiteman et al. |
| 9,931,540 B1 | 4/2018 | Lazar et al. |
| 10,004,937 B2 | 6/2018 | Matsuura et al. |
| D827,061 S | 8/2018 | Trenkle |
| 10,076,460 B2 | 9/2018 | Harry et al. |
| 10,118,063 B2 | 11/2018 | DeYoung |
| 10,124,205 B2 | 11/2018 | Matsuura et al. |
| D836,206 S | 12/2018 | Pettinato et al. |
| 10,143,878 B2 | 12/2018 | Gottfried |
| 10,159,372 B2 | 12/2018 | Heath |
| 10,179,078 B2 | 1/2019 | Bhugra et al. |
| D849,856 S | 5/2019 | Publicover |
| 10,434,357 B2 | 10/2019 | McCarthy |
| 10,653,913 B2 | 5/2020 | Yao et al. |
| D887,502 S | 6/2020 | Nadia |
| 10,702,740 B2 | 7/2020 | Tarkington et al. |
| D895,738 S | 9/2020 | Ying |
| D904,537 S | 12/2020 | Grbic et al. |
| 10,946,247 B1 | 3/2021 | Burton |
| D921,778 S | 6/2021 | Grbic et al. |
| 11,173,344 B2 | 11/2021 | Stehlik |
| D942,565 S | 2/2022 | Hu |
| D969,242 S | 11/2022 | Ehrenreich |
| D982,107 S | 3/2023 | Lu |
| 2002/0165069 A1 | 11/2002 | Ravikumar et al. |
| 2002/0193210 A1 | 12/2002 | Turner |
| 2003/0060339 A1 | 3/2003 | Ravikumar et al. |
| 2004/0084249 A1 | 5/2004 | Rawlings et al. |
| 2004/0087419 A1 | 5/2004 | Ware et al. |
| 2005/0251067 A1 | 11/2005 | Terry |
| 2005/0261113 A1 | 11/2005 | Wilkinson |
| 2006/0103219 A1 | 5/2006 | Sardana |
| 2006/0122040 A1 | 6/2006 | Nguyen et al. |
| 2006/0276736 A1 | 12/2006 | Devreese |
| 2007/0135279 A1 | 6/2007 | Purdy et al. |
| 2008/0083055 A1 | 4/2008 | Onda |
| 2009/0192024 A1 | 7/2009 | Wu |
| 2010/0145233 A1 | 6/2010 | Zhang et al. |
| 2010/0222180 A1 | 9/2010 | Takizawa |
| 2010/0323859 A1 | 12/2010 | von Hoffmann et al. |
| 2011/0046524 A1 | 2/2011 | Mihara et al. |
| 2011/0077560 A1 | 3/2011 | Jacofsky et al. |
| 2011/0111927 A1 | 5/2011 | Kim |
| 2011/0112447 A1 | 5/2011 | Hsiao-Wecksler et al. |
| 2011/0172578 A1 | 7/2011 | Chiu et al. |
| 2011/0314590 A1 | 12/2011 | Perron et al. |
| 2012/0208678 A1 | 8/2012 | Knilans |
| 2013/0041302 A1 | 2/2013 | Williams |
| 2013/0079686 A1 | 3/2013 | Sessions |
| 2013/0184617 A1 | 7/2013 | Naba |
| 2013/0237386 A1 | 9/2013 | Tsai |
| 2014/0179497 A1 | 6/2014 | von Hoffmann et al. |
| 2014/0196190 A1 | 7/2014 | Brown |
| 2014/0302971 A1 | 10/2014 | Gray |
| 2014/0325732 A1 | 11/2014 | Anderson |
| 2014/0336009 A1 | 11/2014 | Piaget et al. |
| 2015/0038885 A1* | 2/2015 | Zhao .................. A61N 1/18 601/22 |
| 2015/0165260 A1 | 6/2015 | Tarkington et al. |
| 2015/0223526 A1 | 8/2015 | Nolan |
| 2015/0314157 A1 | 11/2015 | Lampert et al. |
| 2016/0095367 A1 | 4/2016 | Curran |
| 2016/0183606 A1 | 6/2016 | Shriver |
| 2016/0199689 A1 | 7/2016 | Irwin et al. |
| 2016/0256732 A1* | 9/2016 | Kasner ............... A63B 23/1281 |
| 2016/0279012 A1 | 9/2016 | Hurtado |
| 2016/0361222 A1 | 12/2016 | Publicover et al. |
| 2017/0072250 A1 | 3/2017 | Heiskanen |
| 2017/0246501 A1 | 8/2017 | Palmer |
| 2017/0246502 A1 | 8/2017 | Palmer |
| 2017/0246503 A1 | 8/2017 | Palmer |
| 2017/0252601 A1 | 9/2017 | McKenzie |
| 2017/0274249 A1 | 9/2017 | Moebius et al. |
| 2017/0361151 A1 | 12/2017 | Mottern |
| 2018/0093121 A1 | 4/2018 | Matsuura et al. |
| 2018/0093122 A1 | 4/2018 | Stevenson et al. |
| 2018/0098707 A1 | 4/2018 | Salamon et al. |
| 2018/0104536 A1 | 4/2018 | Stewart |
| 2018/0111016 A1 | 4/2018 | Brockway, Jr. et al. |
| 2018/0207477 A1 | 7/2018 | Barel |
| 2019/0001176 A1 | 1/2019 | Gustafson |
| 2019/0029336 A1 | 1/2019 | Collins et al. |
| 2019/0160322 A1 | 5/2019 | McCarthy |
| 2020/0086170 A1 | 3/2020 | Tarkington et al. |
| 2020/0086172 A1 | 3/2020 | Tarkington et al. |
| 2021/0038943 A1 | 2/2021 | Tarkington et al. |
| 2021/0361999 A1 | 11/2021 | Tarkington et al. |
| 2022/0118311 A1 | 4/2022 | Tarkington et al. |

FOREIGN PATENT DOCUMENTS

| | | |
|---|---|---|
| DE | 20221403 U1 | 11/2005 |
| EP | 2854958 | 4/2015 |
| EP | 2854958 A1 | 4/2015 |
| EP | 008833388-003 | 1/2022 |
| FR | 3024838 A3 | 2/2016 |
| GB | 2372458 A | 8/2002 |

(56) References Cited

FOREIGN PATENT DOCUMENTS

| | | | | |
|---|---|---|---|---|
| GB | 2404877 | | 2/2005 | |
| GB | 2404877 A | | 2/2005 | |
| GB | 2460039 A | * | 11/2009 | ........... A61F 5/0127 |
| GB | 2460039 A | | 11/2009 | |
| JP | 2009254700 | | 11/2009 | |
| JP | 2009254700 A | | 11/2009 | |
| KR | 20140132322 A | * | 11/2014 | ............. A63B 23/08 |
| WO | 2009128565 | | 10/2009 | |
| WO | 2009128565 A1 | | 10/2009 | |
| WO | 2013035905 A1 | | 3/2013 | |
| WO | 2013101920 | | 7/2013 | |
| WO | 2013181063 | | 12/2013 | |
| WO | 2013181063 A1 | | 12/2013 | |
| WO | 2015196190 | | 12/2015 | |
| WO | 2019164633 A2 | | 8/2019 | |
| WO | 2019194885 A1 | | 10/2019 | |

OTHER PUBLICATIONS

International Search Report and Written Opinion in PCT Appln No. PCT/US2013/042441, dated Sep. 6, 2013.
Office Action in CA Appln No. 2,874,237, dated Dec. 10, 2015.
Communication in EP Appln No. 13727007.0, dated Mar. 20, 2017.
International Search Report in PCT Appln No. PCT/US2019/015031, dated Aug. 30, 2019.
International Search Report in PCT Appln No. PCT/US2019/015030, dated Jul. 1, 2019.
Notice of Allowance in U.S. Appl. No. 16/570,742, dated Mar. 3, 2020.
Design U.S. Appl. No. 29/724, 141, filed Feb. 12, 2020, 37 pages.
Design U.S. Appl. No. 29/746,283, filed Aug. 22, 2020, 62 pages.
U.S. Appl. No. 16/918,671, filed Jul. 1, 2020, 111 pages.
U.S. Appl. No. 17/045,257, filed Oct. 5, 2020, 93 pages.
Notice of Refusal in Korean Patent Application No. 30-2020-00306898 dated Sep. 3, 2021 and Aug. 30, 2021.
Final Office Action dated Feb. 1, 2022 in U.S. Appl. No. 29/724,141.
Notice of Allowance dated Feb. 4, 2022 in U.S. Appl. No. 16/918,671.
Notice of Allowance dated Dec. 3, 2021in Mexican Application No. MX/f/2020/001920.
Examination report dated Feb. 15, 2022 in Canadian Application No. 209921.
Related U.S. Appl. No. 16/570,817 entitled Portable Devices for Exercising Muscles in the Ankle Foot andor Leg and Related Methods, filed Sep. 13, 2019.
Office Action for U.S. Appl. No. 16/570,817, dated May 13, 2021.
Notice of Allowance dated Aug. 19, 2021 in connection with U.S. Appl. No. 16/570,817, 12 pp.
Office Action dated Oct. 12, 2021 in related U.S. Appl. No. 29/724,141, 12 pages.
FF Finer form store, announced 2018 [online], [site visited Dec. 6, 2021]. Available on internet, URL:https://www.amazon.com/ Finer-Form-Multi-Functional-Bench-Workout/dp/B07GYXF65S/ref=sr_1_196_sspa?dchild=1&keywords=adjustable+ankle+and-foot +board &qid=1633368733&sr=8-196-spons&psc=1 (Year: 2018).
Office Action dated Oct. 13, 2021 in related U.S. Appl. No. 16/918,671, 11 pages.
Barwing, announced 2020[online], [site visited Dec. 6, 2021]. Available on internet, URL:https://www.amazon.com/dp/B07WDHNKKB/ref=sspa_dk_detail_1?psc=1&pd_rd_i=B07WDHNKKB&pd_rd_w=ovafF&pf_rd_p=9fd3ea7c-b77c-42ac-b43b-c872d3f37c38&pd_rd_wg=K4R8E&pf_rd_r=QGNJ4V8P6PRKQYFAPHRE&pd_rd_r=c9b8a389 (Year: 2020).
U.S. Pat. No. 0735319 to A.W. Urwick, dated Aug. 4, 1903.
Examination report dated Dec. 7, 2021 for CA app No. 197544.
Office Action dated Dec. 21, 2021 in related U.S. Appl. No. 17/045,257, 16 pages.
U.S. Appl. No. 17/562,682, filed Dec. 27, 2021.
Notice of Allowance dated Apr. 19, 2022 in U.S. Appl. No. 29/724, 141.
Notice of Allowance dated Apr. 26, 2022 in Korean Application No. 30-2020-0036898.
Final Office Action dated Jul. 6, 2022 in U.S. Appl. No. 17/045,257, 15 pp.
Notice of Allowance dated Aug. 26, 2022 in Mexican Application No. MX/a/2021/003732.
Notice of Allowance dated Oct. 14, 2022 in U.S. Appl. No. 17/562,682, 13 pages.
"Revbalance FIT 3-in-1 Exercise Balance Board," Aug. 29, 2015, Amazon, site visited Dec. 14, 2022: https://amzn.to/3FxwrOf (Year: 2015).
"FluidStance," Jun. 7, 2019, Youtube, site visited Dec. 14, 2022: https://www.youtube.com/watch?v=U4gnZLAsayM (Year: 2019).
"LifePro Rumblex Max 4D Vibration Plate," Jul. 19, 2020, Amazon, site visited Dec. 14, 2022: https://amzn.to/3WdEhoK (Year: 2020).
Notice of Allowance dated Dec. 22, 2022 in U.S. Appl. No. 17/045,257.
Office Action dated Apr. 14, 2023 in Design U.S. Appl. No. 29/746,283.
"Bluefin Fitness Dual Motor" May 3, 2018, Amazon, site visited Apr. 7, 2023: https://www.amazon.com/dp/B0792YG7LQ (Year: 2018 ).
"AXV Vibration Plate Exercise Machine" Jul. 1, 2021, Amazon, site visited Apr. 7, 2023: https://www.amazon.com/AXV-Vibration-Exercise-Platform-Wellness/dp/B098FFTRMK (Year: 2021).
Office Action dated Jun. 5, 2023 in related Patent Application No. 19721406.7.
"Lifepro Waver Mini Vibration Plate" Mar. 13, 2020, Amazon, site visited Aug. 3, 2023: https://www.amazon.com/dp/B085WB14JW (Year: 2020).
"Revbalance Focus—Standing Desk Balance Board" Aug. 8, 2017, Amazon, site visited Aug. 3, 2023: https://www.amazon.com/dp/B074N9ZMV8 (Year: 2017).
Notice of Allowance dated Aug. 23, 2023 in Design U.S. Appl. No. 29/746,283, 7 pages.

* cited by examiner

DEVICES AND METHODS FOR EXERCISING AN ANKLE, FOOT, AND/OR LEG

CROSS-REFERENCE TO RELATED APPLICATIONS

This application is a U.S. national stage application under 35 U.S.C. § 371(c) of International Application No. PCT/US2019/015031, filed Jan. 24, 2019, which claims priority to U.S. Provisional Patent Application No. 62/635,165, filed Feb. 26, 2018 and entitled "Devices and Methods for Exercising an Ankle, Foot, and/or Leg," and to U.S. Provisional Patent Application No. 62/731,514, filed Sep. 14, 2018 and entitled "Devices and Methods for Exercising an Ankle, Foot, and/or Leg," the entire content of each of which is incorporated by reference herein.

TECHNICAL FIELD

The present disclosure relates to devices and methods for exercising an ankle, foot and/or leg. More particularly, the present disclosure relates to devices and methods for exercising muscles in the ankle, foot, and/or leg of a user to increase blood circulation, which may, for example, assist in preventing venous thromboembolism.

INTRODUCTION

The section headings used herein are for organizational purposes only and are not to be construed as limiting the subject matter described in any way.

Venous thromboembolism (VTE) occurs when red blood cells, fibrin and, to a lesser extent, platelets and leukocytes, form a mass (i.e., a clot) within an intact vein. The thrombus (i.e., blood clot) is referred to as a deep venous thrombosis (DVT) when formed within the deep veins of the legs or in the pelvic veins. A pulmonary embolism (PE) results when a piece of thrombus detaches from a vein wall, travels to the lungs, and lodges within the pulmonary arteries.

VTE is often a concern in situations where an individual is immobile and/or relatively non-ambulatory for a period of time, such as, for example, during hospitalization, after surgery, during pregnancy and/or in the postpartum period, while traveling (e.g., in a car, a plane and/or a train), at work, and/or in a more sedentary lifestyle (e.g., the elderly and/or obese). Blood returning to the heart does so through veins. Large veins, such as those found in the legs, lie near and between muscles and contain valves that maintain the flow of blood in the direction of the heart by preventing backflow and stasis. The contraction of these muscles (e.g., through walking) forces the blood through the veins in the direction of the heart, usually against the force of gravity, thereby preventing blood from accumulating in the extremities. However, if these muscles are not used and/or are minimally or infrequently used for an extended period of time, the lower limbs may swell with stationary blood, greatly increasing the risk of VTE.

Because of this potential danger, preventative measures against VTE have become standard, for example, in prolonged hospitalizations and postoperative care. Consequently, in conjunction with early ambulation, a number of other prophylaxis devices have been developed to help prevent VTE. Graduated compression stockings, for example, gradually apply a decreasing amount of pressure as a stocking moves up a leg (i.e., from ankle to thigh), help to squeeze or push venous blood up the leg in an effort to counteract pooling. Such stockings, although inexpensive, are difficult to put on and take off a patient, generally requiring medical staff assistance to do so, and use of these stockings may present an even greater challenge in outpatient settings, where assistance is not readily available. Intermittent pneumatic compression devices, which generally comprise a cuff that slides over the leg, provide undulating compression to the calf muscle to help drive blood from the leg back to the heart. Such devices, however, are expensive and cumbersome, and are in some cases stored in a central storeroom and, thus, are not readily available on the hospital floor and/or outside of a clinical medical setting. Pneumatic compression devices also require significant medical staff assistance for setup, which requirement is exacerbated by the need to disconnect the unit anytime the patient is moved, resulting in poor compliance with the prophylaxis regime. Furthermore, since compressive techniques fail to treat and articulate a patient's ankle and/or knee joints, or otherwise contract the ankle, foot and/or leg (e.g., calf) muscles, such devices have limited exercise and therapy capabilities and/or benefits, and are, therefore, impractical for use outside of a hospital setting.

Various additional exercise devices serve to articulate a patient's joints, thereby providing joint therapy while contracting the muscles of the ankle, foot, and/or leg to prevent blood from accumulating in the lower extremities of the body. Some such devices, however, may be difficult for non-ambulatory patients to use as they may require, for example, a patient to remain in an upright or a standing position while exercising the leg/ankle and without additional leg support. Furthermore, such devices generally do not provide for a full range of ankle flexion and extension, that is, such devices do not provide both plantar flexion (i.e., movement which increases the approximate 90° angle between the front part of the foot and the shin, thereby contracting the calf muscle) and dorsiflexion motion (i.e., movement which decreases the angle between the front part of the foot and the shin, thereby stretching the calf muscle). Many of these conventional devices are also cumbersome, complex and expensive. And conventional devices may be impractical for use during transition care or between care locations, or for use by other VTE at-risk groups (e.g., travelers).

Due to growing concerns over the continued prevalence of VTE-related medical cases, it may be desirable to provide a relatively simple, inexpensive device and method with full exercise and therapy capabilities and/or benefits, which provides for a full range of ankle flexion and extension to increase blood circulation in the lower extremities of the body. It may also be desirable to provide a device and method that is simple to use and therefore promotes continuous use of the device, provides an effective visual link as a reminder to perform desired exercises, and/or that transitions relatively seamlessly between inpatient and outpatient settings. It also may be desirable to provide a device that is portable and, thus, accessible, to all VTE at-risk individuals. It may further be desirable to provide a device and method that can be relatively easily used by individuals having varying levels of strength, coordination, and/or balance.

SUMMARY

The present disclosure may solve one or more of the above-mentioned problems and/or may demonstrate one or more of the above-mentioned desirable features. Other features and/or advantages may become apparent from the description that follows.

In accordance with various exemplary embodiments of the present disclosure, an exercise device comprises a foot support portion pivotably connected to a leg support portion and having a neutral position relative to a pivot axis. The support portion is configured to rotate about the pivot axis in a first direction away from the neutral position and in a second direction away from the neutral position. The second direction is opposite the first direction. The exercise device also includes a resistance mechanism configured to exert a force on the foot support portion about the pivot axis opposite to the respective first and second directions of rotation of the foot support portion about the pivot axis.

In accordance with various additional exemplary embodiments of the present disclosure, an exercise device comprises a foot support portion connected to a leg support portion. The foot support portion is configured to receive a foot of a user and to rotate with respect to the leg support portion throughout a full range of ankle flexion and extension of a foot positioned in the foot support portion. The exercise device also comprises a resistance mechanism configured to resist rotation of the foot support portion throughout an entire range of motion of the foot support portion by exerting a constant force in a direction opposite to the rotation of the foot support portion.

In accordance with various further exemplary embodiments of the present disclosure, an exercise device comprises a first support portion pivotably connected to a second support portion and having a neutral position relative to a pivot axis. The first support portion is configured to rotate about the pivot axis in a first direction away from the neutral position and in a second direction away from the neutral position. The second direction is opposite the first direction. The exercise device further comprises a resistance mechanism configured to exert a force on the first support portion about the pivot axis opposite to the respective first and second directions of rotation of the first support portion about the pivot axis.

In accordance with various additional exemplary embodiments of the present disclosure, a method for exercising muscles in an ankle, foot, and/or leg of a user comprises, with a foot of the user positioned on a foot support portion of an exercise device, rotating the foot support portion relative to a leg support portion of the exercise device in a first direction about a pivot axis of the exercise device and against a force exerted by a resistance mechanism of the exercise device in a second direction of rotation, opposite to the first direction of rotation. The method further comprises, with the foot of the user positioned on the foot support portion of the exercise device, rotating the foot support portion relative to the leg support portion in the second direction of rotation about the pivot axis and against a force exerted by the resistance mechanism in the first direction of rotation.

In accordance with various additional exemplary embodiments of the present disclosure, a method for exercising muscles comprises, with a body part of a user positioned on a first support portion of an exercise device, rotating the first support portion relative to a second support portion of the exercise device in a first direction of rotation about a pivot axis of the exercise device and against a force exerted by a resistance mechanism of the exercise device in a second direction of rotation, opposite to the first direction of rotation. The method also comprises rotating the first support portion relative to the second support portion in the second direction of rotation about the pivot axis and against a force exerted by the resistance mechanism in the first direction of rotation.

In accordance with various further exemplary embodiments of the present disclosure, a method for exercising muscles in an ankle, foot, and/or leg of a user comprises increasing circulation velocity within body tissue by, with a foot of the user positioned on a foot support portion of an exercise device, rotating the foot support portion relative to a leg support portion of the exercise device in a first direction of rotation about a pivot axis of the exercise device and against a force exerted by a resistance mechanism of the exercise device in a second direction of rotation, opposite to the first direction of rotation. The method also comprises rotating the foot support portion relative to the leg support portion in the second direction of rotation about the pivot axis and against a force exerted by the resistance mechanism in the first direction of rotation. The body tissue may comprise blood vessels and/or muscles.

Additional objects and advantages will be set forth in part in the description which follows, and in part will be obvious from the description, or may be learned by practice of the present disclosure. The objects and advantages may be realized and attained by means of the elements and combinations particularly pointed out in the appended claims and their equivalents.

It is to be understood that both the foregoing general description and the following detailed description are exemplary and explanatory only and are not restrictive of the present disclosure and claims.

BRIEF DESCRIPTION OF THE DRAWINGS

The present disclosure can be understood from the following detailed description either alone or together with the accompanying drawings. The drawings are included to provide a further understanding and are incorporated in and constitute a part of this specification. The drawings illustrate one or more exemplary embodiments of the present disclosure and together with the description serve to explain various principles and operations.

DESCRIPTION OF VARIOUS EXEMPLARY EMBODIMENTS

Figure 1:
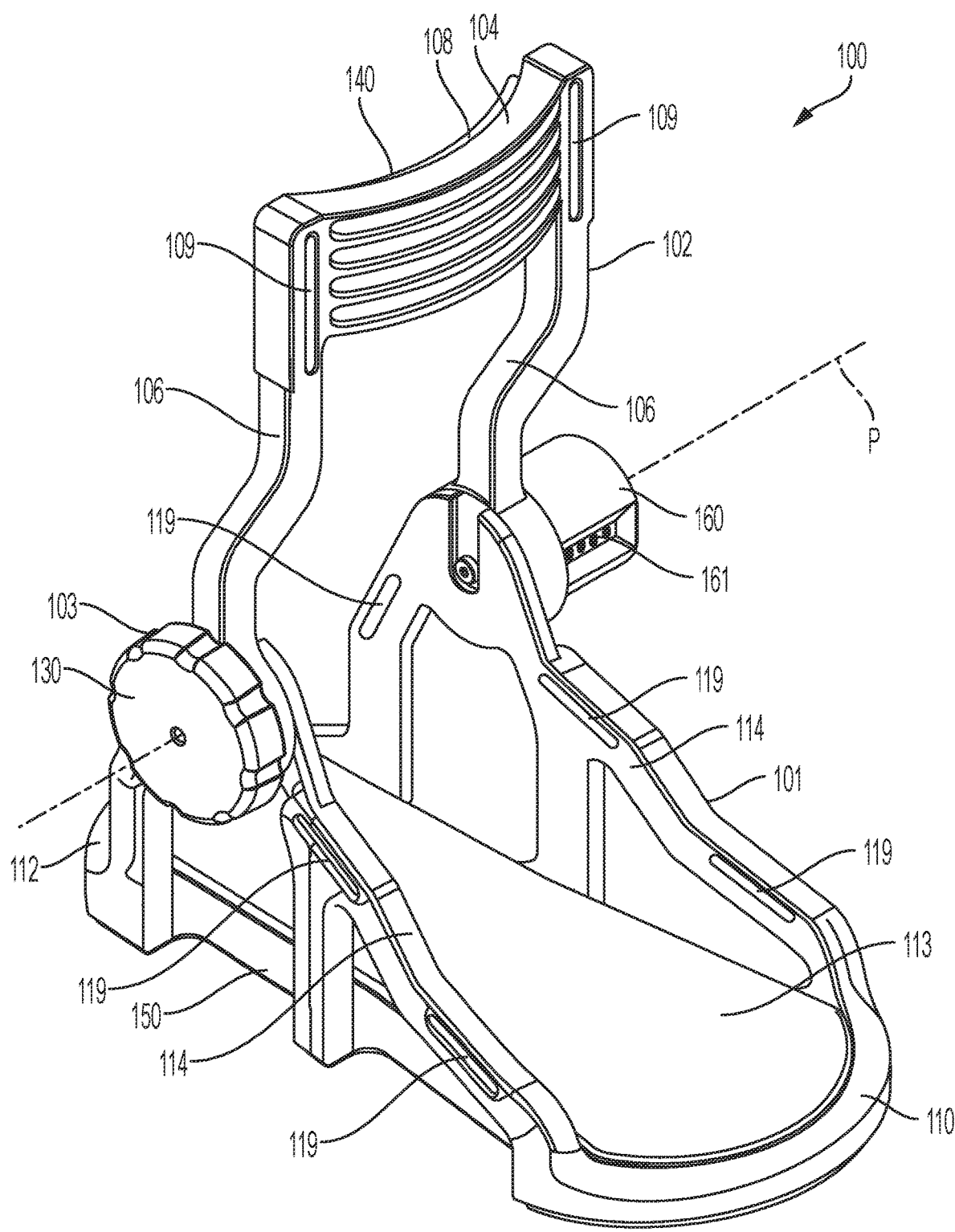
FIG. 1 is a perspective front view of an exemplary embodiment of an exercise device in accordance with the present disclosure.
Figure 2:
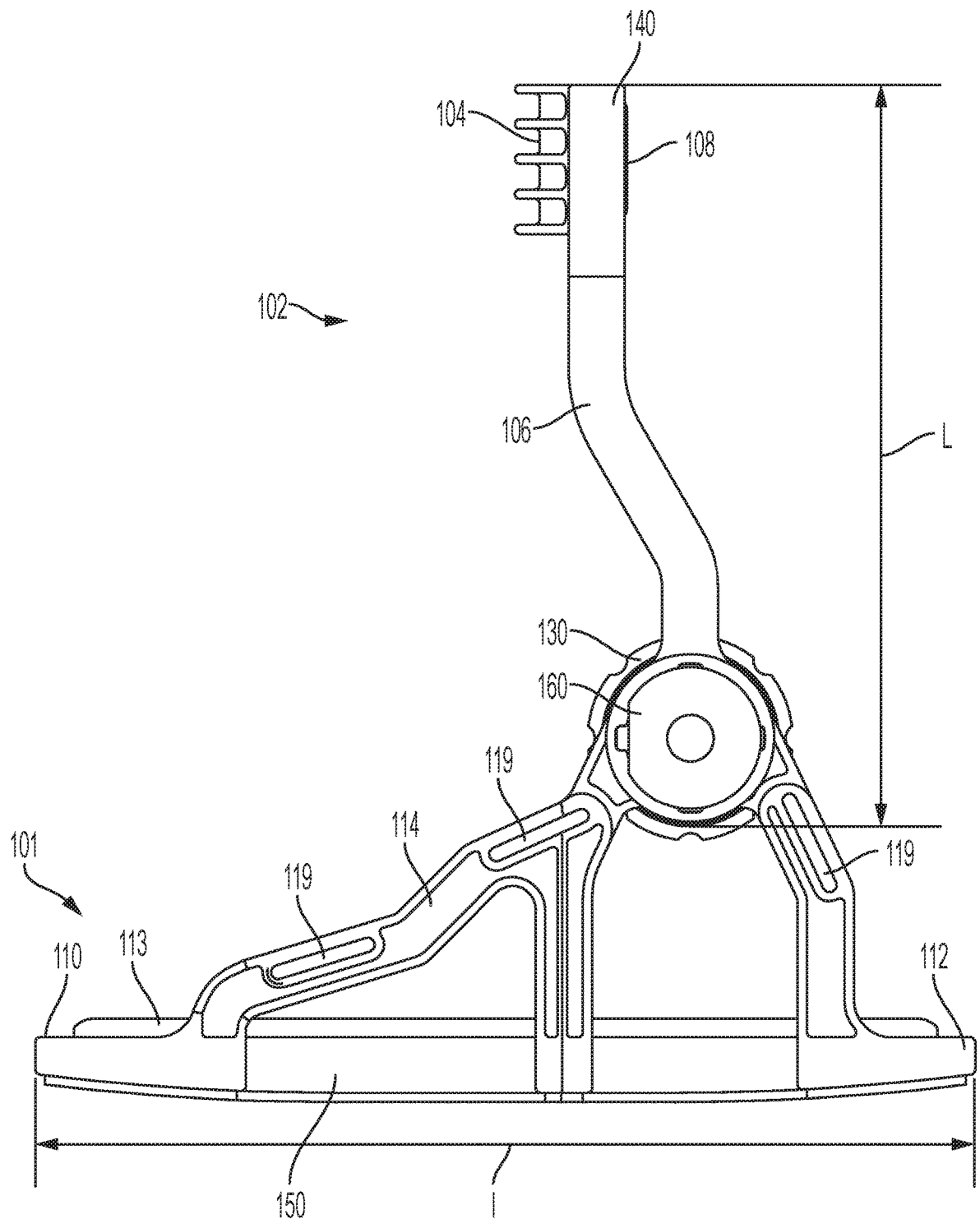
FIG. 2 is a left side view of the device of FIG. 1.
Figure 3:
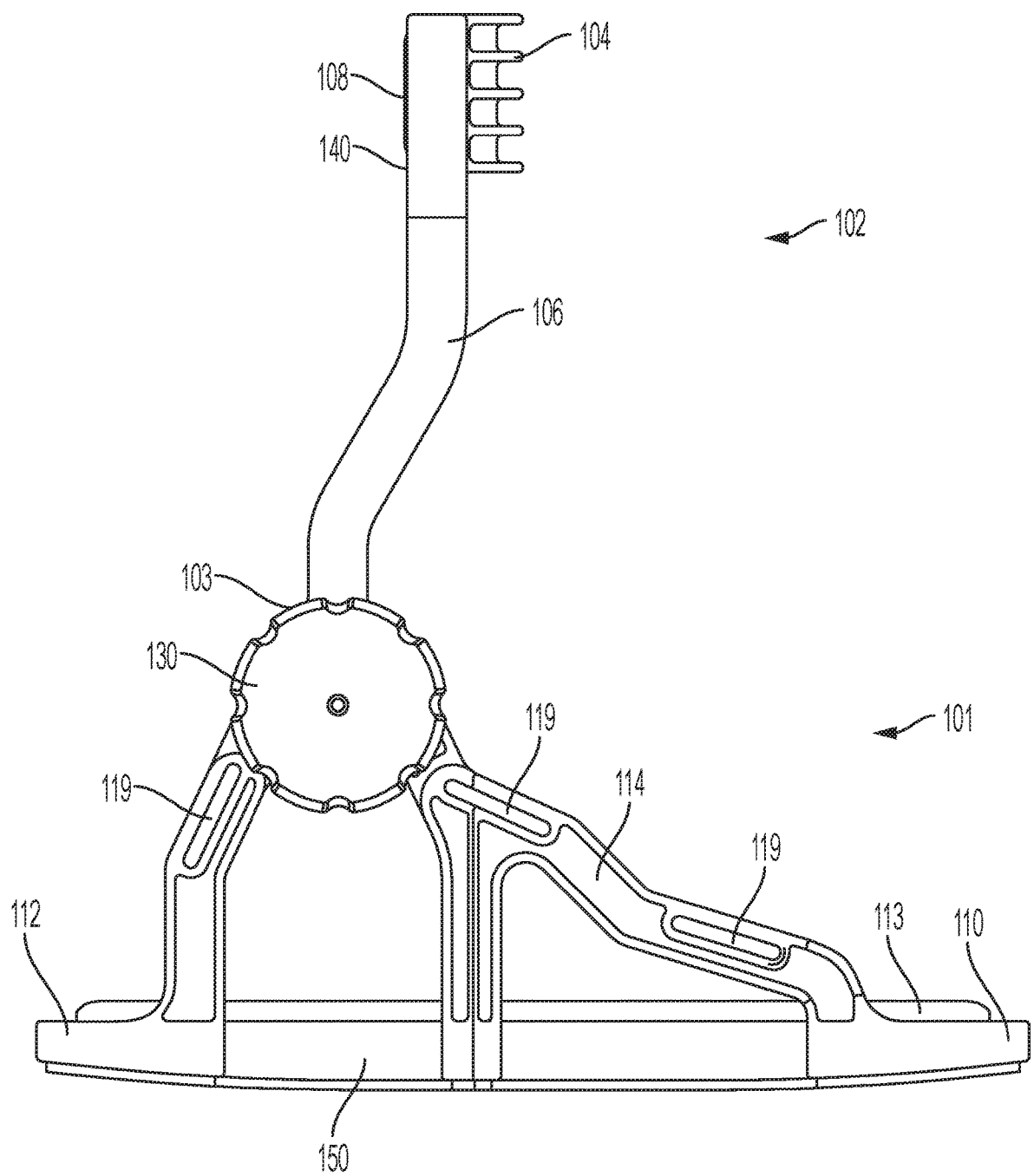
FIG. 3 is a right side view of the device of FIG. 1.

Various conventional thromboprophylactic techniques typically rely on devices that are cumbersome, complex, and/or expensive. Consequently, such devices may be underutilized during hospitalization and become impractical for use during transition care or between care locations, or for use by other vulnerable groups, such as, for example, travelers and/or other individuals sitting or lying for extended periods. Furthermore, such devices, are generally limited to the specific purpose of VTE prevention and do not have practical use for other common exercise applications, such as, for example, ankle rehabilitation, which may require a device allowing for a broader range of movement. To increase thromboprophylactic utilization, various exemplary embodiments of the present disclosure provide devices and methods of exercising an ankle, foot and/or leg that provide simple and relatively inexpensive prophylaxis by providing for a full range of ankle flexion and extension to increase circulation in the lower extremities of the body. Increasing circulation may include increasing circulation in body tissues. Movement of bodily fluids, including blood, lymph, and/or interstitial fluids may be achieved through practice of the disclosed methods and use of the disclosed devices. The increased circulation may be found in one or more of blood vessels, the lymphatic system, muscles, interstitial spaces, capillaries and surrounding body tissues. In addition to the movement of fluids through ankle flexion and extension, the pressure applied to the sole of the foot during the exercise, i.e., plantar pressure, also contributes to movement of fluid through the body tissue and to an increase in circulation of bodily fluids.

In various exemplary embodiments, exercise devices and methods for exercising an ankle, foot and/or leg use a foot support portion that is pivotably connected to a leg support portion and having a neutral position relative to a pivot axis, the foot support portion being configured to rotate about the pivot axis in a first direction and a second direction opposite the first direction, wherein the second direction is opposite the first direction.

The devices and methods further use a resistance mechanism that is configured to exert a force on the foot support portion about the pivot axis opposite to the respective first and second directions of rotation of the foot support portion about the pivot axis. For example, in accordance with various embodiments, to continuously exercise the ankle, foot, and/or leg of the user throughout the complete range of ankle flexion and extension, as explained further below, the force exerted by the resistance mechanism is configured to provide a continuous passive resistance to the rotational movement of the foot support portion. In other words, the resistance mechanism is configured to provide a passive resistance against the rotation of the foot support portion throughout a full range of ankle flexion and extension of a user's foot, without, for example, the need for user interaction to resist the force exerted by the resistance mechanism. For example, in various exemplary embodiments, the resistance mechanism may provide a constant force throughout an entire range of motion of the foot support portion.

Figure 13:
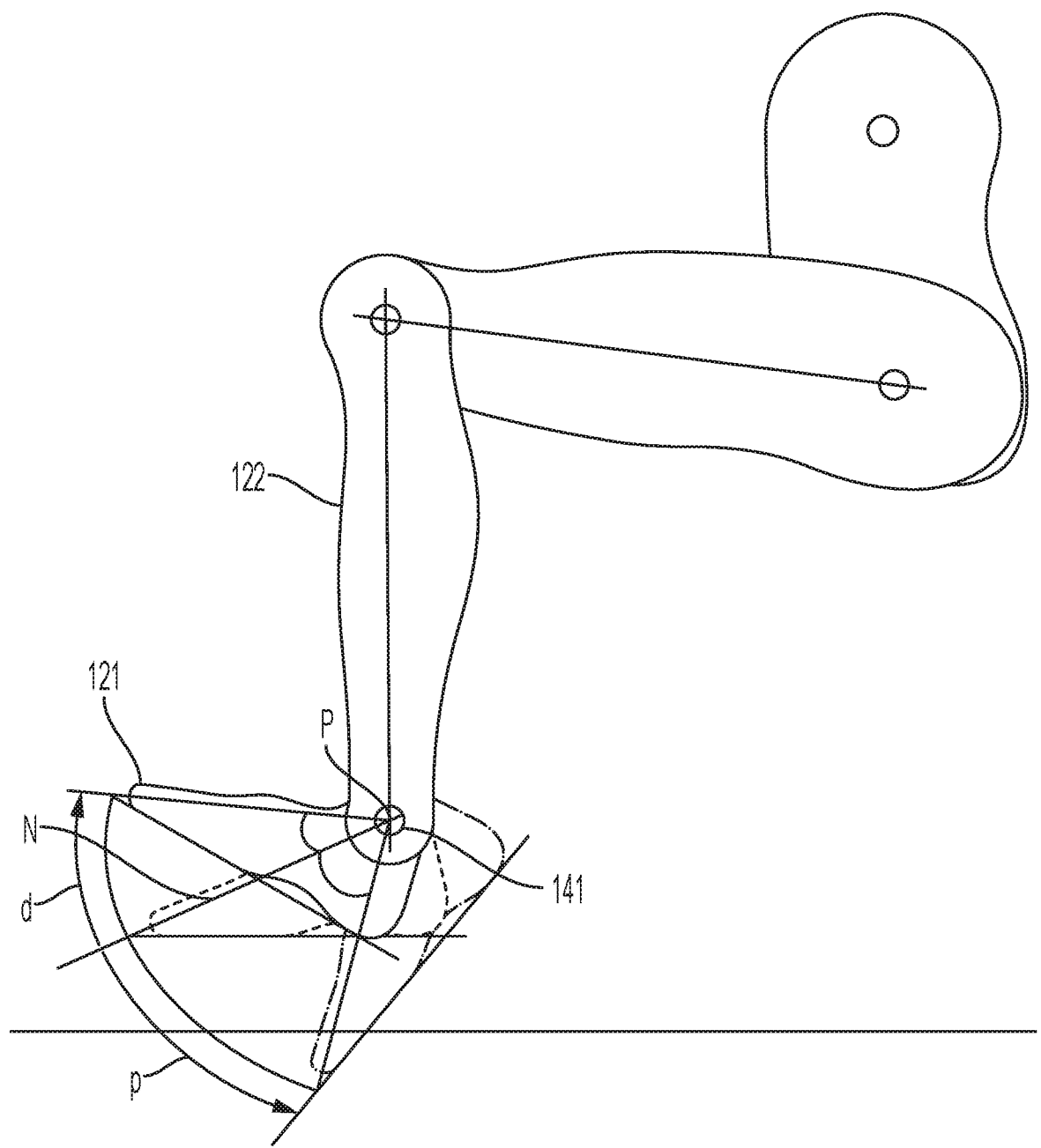
FIG. 13 is a diagram of an exemplary range of motion of the exercise devices in accordance with the present disclosure.

As used herein, the term "full range of ankle flexion and extension" refers to the complete range of motion that the joints of a healthy user's ankle may undergo. In accordance with exemplary embodiments of the present disclosure, as illustrated in FIG. 13, a full range of ankle flexion and extension includes about 75 degrees of plantar flexion motion p (e.g., rotation ranging from about neutral to 75 degrees, or 90 degrees to about 165 degrees from the leg support portion); and about 60 degrees of dorsiflexion motion d (e.g., rotation ranging from about neutral to −60 degrees, or 90 degrees to about 30 degrees from the leg support portion). It will be understood, however, that the ambulatory ability of a user may be limited, and that, accordingly, the range of ankle flexion and extension of each individual user may vary and be somewhat to significantly less than the full range of ankle flexion and extension.

Accordingly, as illustrated in the exemplary embodiments shown in the drawings, an exercise device in accordance with the present disclosure has a simple configuration, which includes three main parts: 1) a leg support portion, 2) a foot support portion pivotably connected to the leg support portion, and 3) a resistance mechanism which is configured to resist the rotation of the foot support portion with respect to a neutral position in two opposite directions. FIG. 1 illustrates an exemplary exercise device 100 in accordance with an exemplary embodiment of the present disclosure. As shown in FIG. 1, the exercise device 100 includes a leg support portion 102, a foot support portion 101, and a resistance mechanism 103. As shown, the foot support portion 101 extends from an end of the leg support portion 102 and is pivotably connected relative to the leg support portion 102, as will be described in further detail below. The leg support portion 102 provides a leg support surface 140 configured to receive and support a leg of a user while the user is using the device 100, and the foot support portion 101 provides a foot support surface 150 configured to receive and support a foot of the user while the user is using the device 100, as will be described in more detail below.

The leg support portion 102 may be formed from any material and/or combination of materials suitable for connecting the foot support portion 101 and for supporting a leg of a user in accordance with the present disclosure. In various exemplary embodiments, the leg support portion 102 may, for example, comprise a molded plastic material, such as, for example, a molded polypropylene material. Those of ordinary skilled in the art will understand, however, that the leg support portion 102 may be made of various plastic materials, as well as various other materials, including, for example, wood and/or metal materials. Suitable materials can include, for example, materials that are relatively light so as to facilitate carrying the device 100, yet durable and able to withstand repetitive use.

As shown in FIGS. 1-9, for example, the leg support portion 102 includes a contoured plate 104 provided with a leg support surface 140 that is configured to receive a leg 122 of a user 123 (see FIGS. 8-10), and a pair of legs 106 that extend downwardly from the contoured plate 104 to connect the plate 104 to the foot support portion 101. As will be understood by those of ordinary skill in the art, the leg support portion 102, including the contoured plate 104 and the legs 106, is appropriately sized and/or configured to accommodate a range of user weights and/or heights (e.g., one size fits all). In various exemplary embodiments, for example, the leg support portion 102 can have a length L (see FIG. 2) ranging from about 7 inches to about 18 inches, for example, about 7 inches to about 10 inches. To more comfortably accommodate various users, in various additional embodiments, the leg support surface 140 of the contoured plate 104 may include a depression 108 that is removably mountable to the plate 104 and comes in multiple sizes. In various embodiments, for example, the depression 108 may be made from a soft, form fitting material, such as, for example, a shape memory polymer, which may form to different users as well as promote hygiene as would be understood by those of ordinary skill in the art.

Figure 8A:
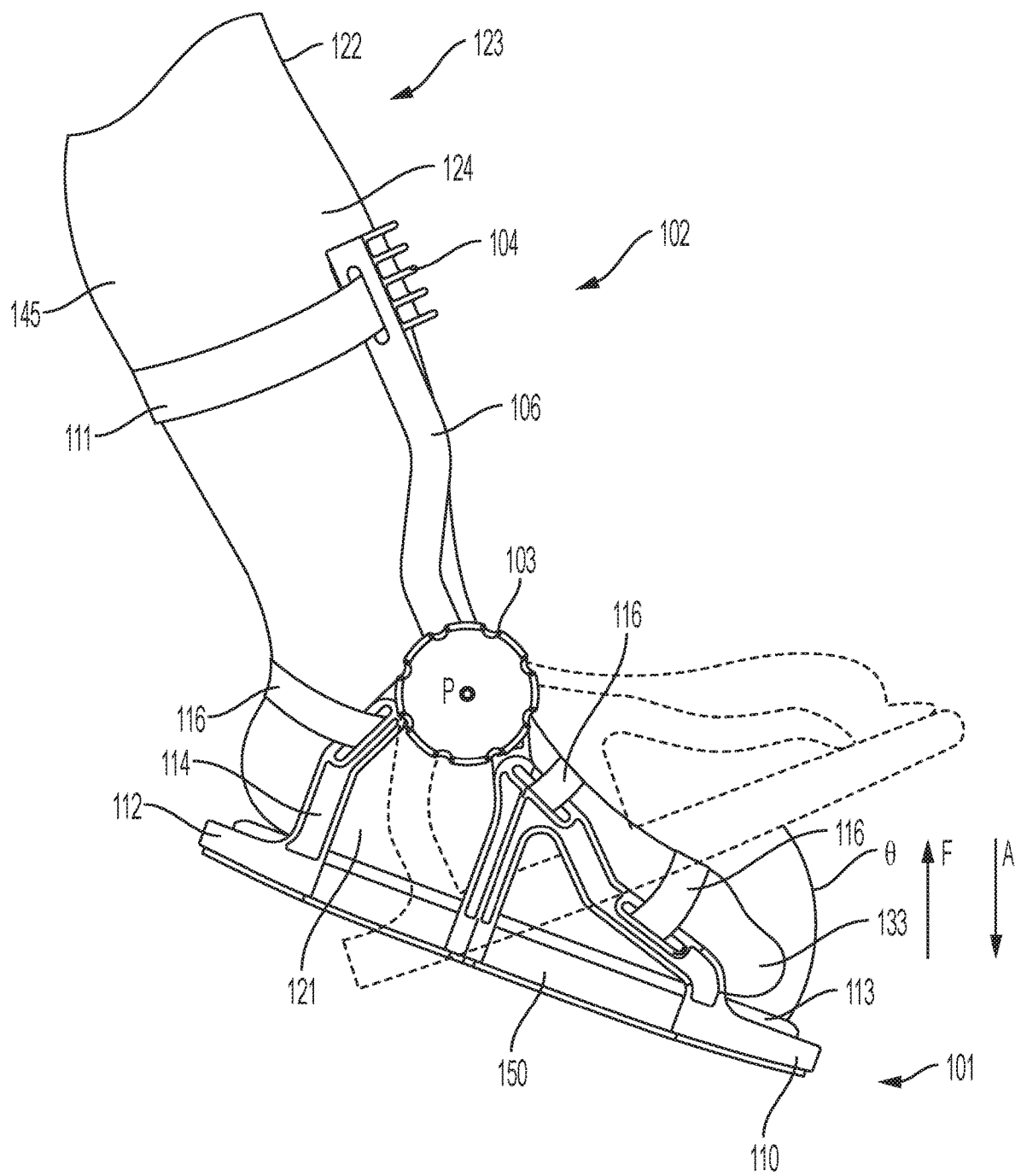
FIG. 8A is a right side view of the device of FIG. 1 showing a user rotating a foot support portion of the device in a first direction.
Figure 8B:
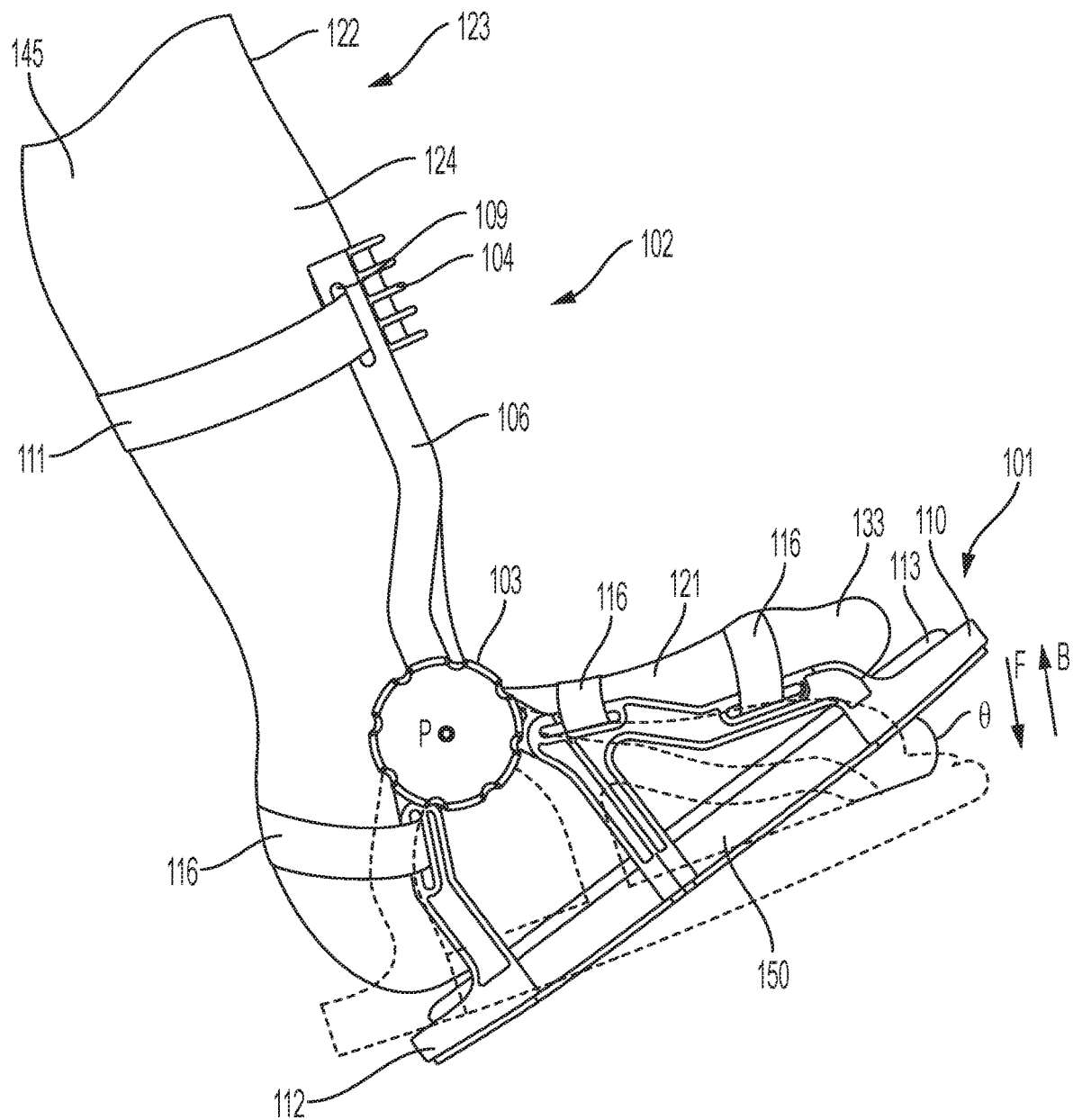
FIG. 8B is a right side view of the device of FIG. 1 showing a user rotating a foot support portion of the device in a second direction.
Figure 9:
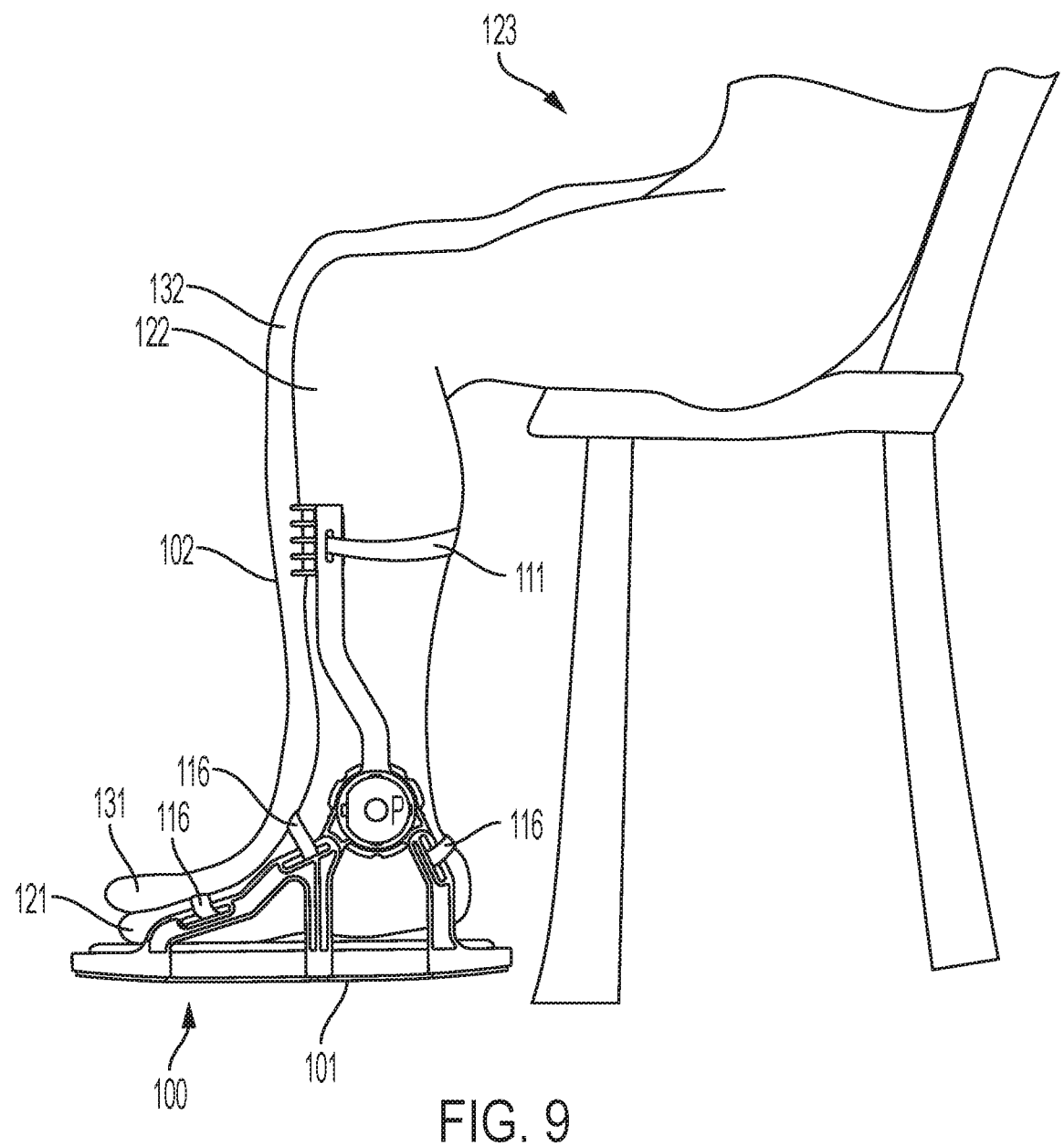
FIG. 9 is a left side view of the device of FIG. 1 showing a user using the device in a sitting position.
Figure 10:
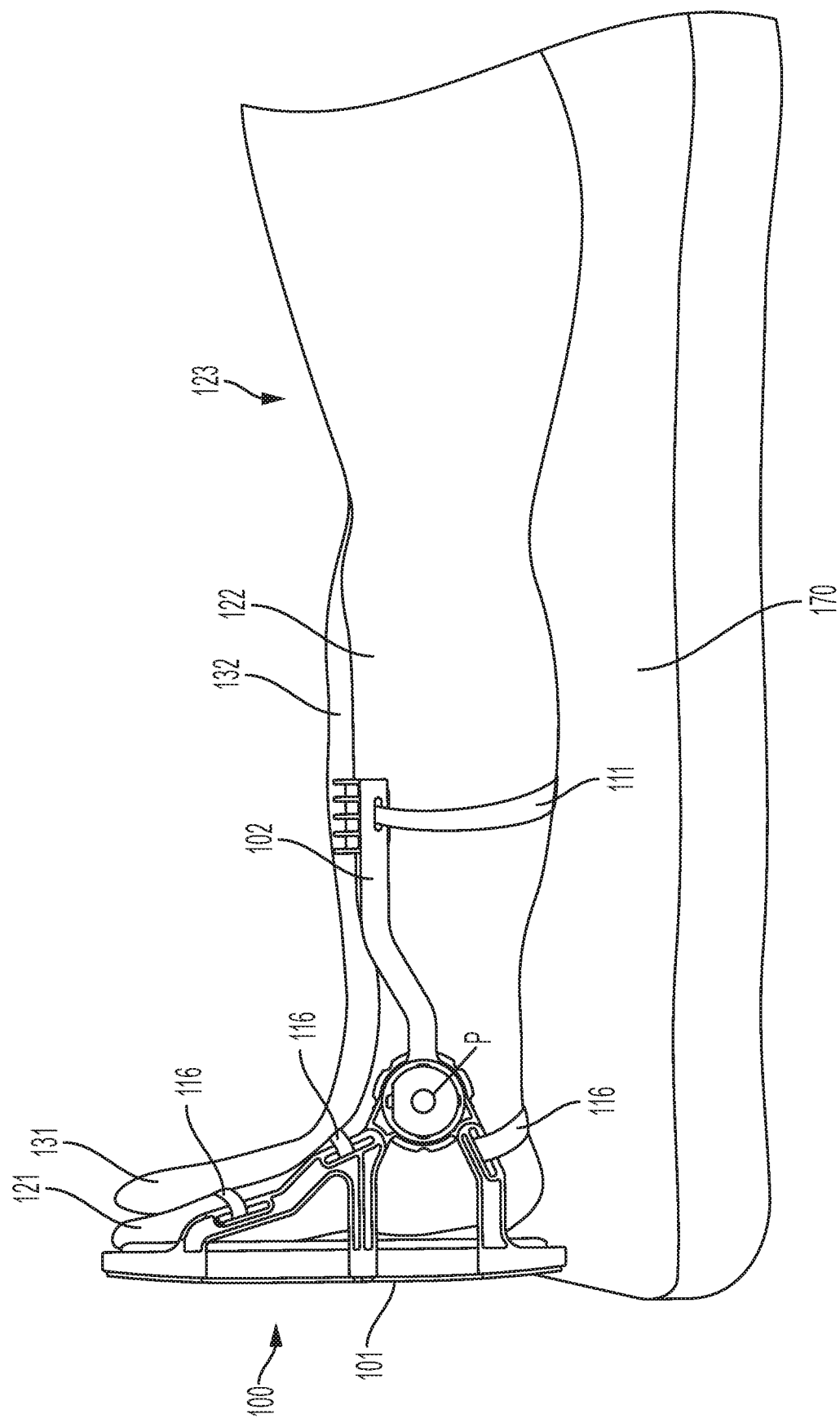
FIG. 10 is a left side view of the device of FIG. 1 showing a user using the device in a supine position.

As shown in FIGS. 8-10, in various exemplary embodiments, the leg support portion 102 also may comprise at least one strap 111 affixed to respective sides of the leg support portion 102 via, for example, slits 109 in each side of the contoured plate 104. The strap 111 may, for example, be configured to releasably secure around the leg 122 of the user 123 to assist in securing the device 100 to the leg 122. By way of example only, in various exemplary embodiments, the strap 111 may comprise hook and loop fasteners, such as, for example, Velcro®. Those of ordinary skill in the art will further understand that the strap 111 may comprise any type and/or configuration of mechanism to releasably secure the leg 122 of the user 123 to the leg support portion 102, including for example, cuffs, snaps, buttons, ties, buckles, elastic bands, sliders, and/or any combination thereof.

Those of ordinary skill in the art will further understand that the leg support portion 102 may have various sizes, shapes, configurations and/or features without departing from the scope of the present disclosure. In various embodiments, for example, the leg support portion 102 may also include various cushioning and/or shock mechanisms to increase user comfort.

The foot support portion 101 may be formed from any material suitable for receiving and/or supporting the foot of a user in accordance with the present disclosure. In various exemplary embodiments, the foot support portion 101 may, for example, comprise a molded plastic material, such as, for example, a molded polypropylene material. Those ordinarily skilled in the art will understand, however, that the foot support portion 101 may be made of various plastic materials, as well as various other materials, including, for example, wood and/or metal materials. Suitable materials can include, for example, materials that are relatively light so as to facilitate carrying the device 100, yet durable and able to withstand repetitive use/motion.

As illustrated in FIGS. 1-10, the foot support portion 101 can be shaped to receive a user's foot, for example, a foot 121 of the user 123 (see FIGS. 8-10). For example, the foot support portion 101 may comprise a sandal (see FIGS. 11 and 12), slipper, shoe, or boot configured to receive the foot 121 of the user 123. The foot support portion 101 can be sized to accommodate a range of foot and/or shoe sizes. In accordance with one aspect of the present disclosure, for example, the foot support portion can have a length l (see FIG. 2) ranging from about 8 inches to about 20 inches, for example ranging from about 12 inches to about 14 inches, and a width w (see FIG. 4) ranging from about 0.5 inches to about 7 inches, for example, about 3 inches to about 5 inches. Additionally, as shown in FIGS. 1-9, the foot support portion 101 includes a foot support surface 150 having a toe end portion 110 and a heel end portion 112, and a framework 114 that extends upwardly from the foot support surface 150 to connect the foot support surface 150 to the leg support portion 102. Those ordinarily skilled in the art will understand, however, that the foot support portion 101 may have various sizes, shapes, configurations and/or features without departing from the scope of the present disclosure. As illustrated in FIGS. 17-20, for example, various exemplary embodiments of the present disclosure contemplate an exercise device 400, 500 including a foot support portion 401, 501 having a contoured foot support surface 450, 550, such that the heel end portion 412, 512 is slightly elevated with respect to a toe end portion 410, 510. In this manner, the foot support surface 450, 550 and framework 414, 514 (i.e., which extends upwardly from the foot support surface 450, 550 to connect the foot support surface 450, 550 to the leg support portion 402, 502) form a contoured boot with a wedge-like heel 460, 560. Various additional embodiments of the present disclosure also contemplate that the foot support portion 101 may comprise a simple blade and/or spring support upon which the user's foot may rest.

Figure 19:
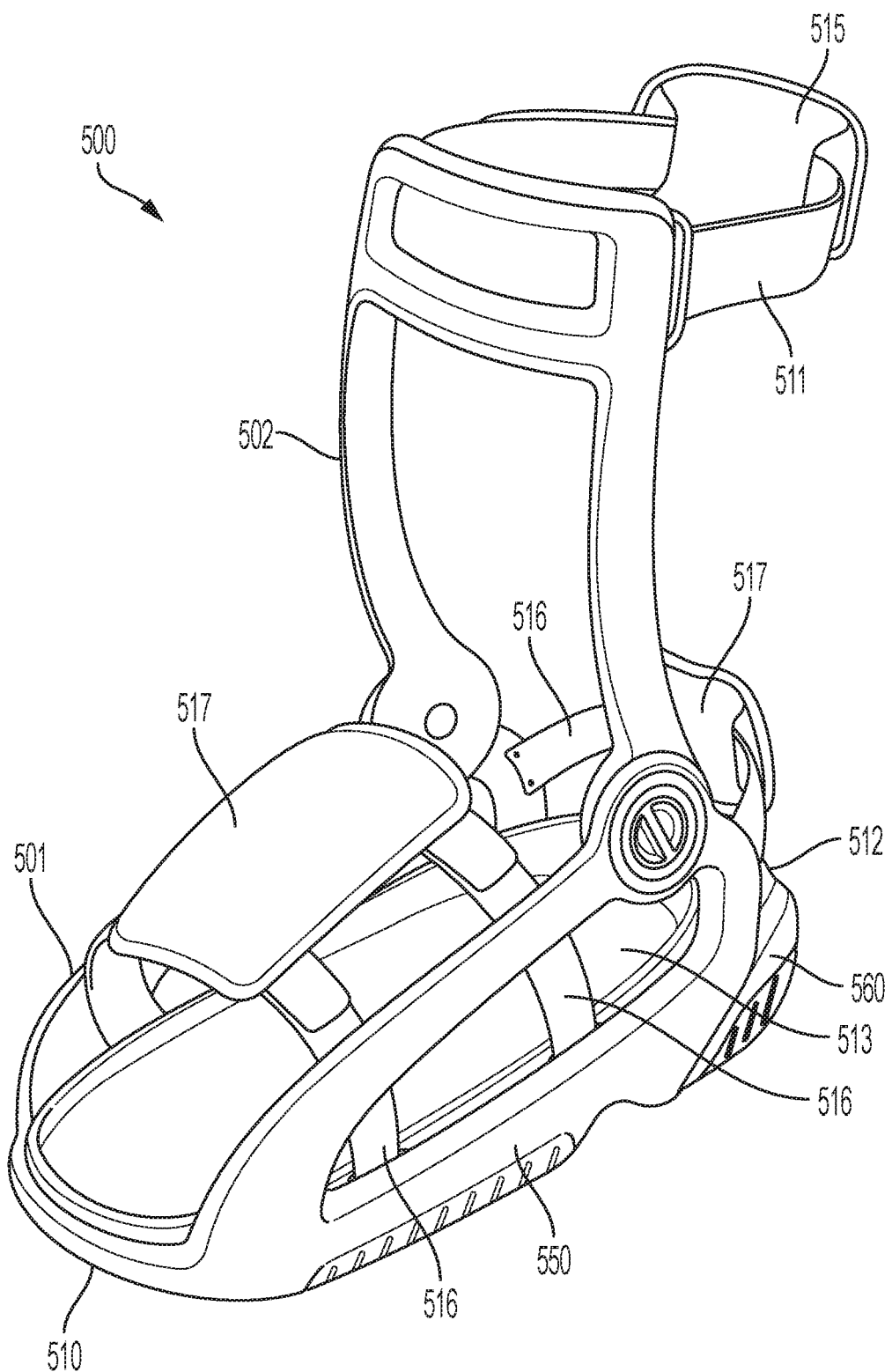
FIG. 19 is a perspective, front left side view of another exemplary embodiment of an exercise device in accordance with the present disclosure.
Figure 20:
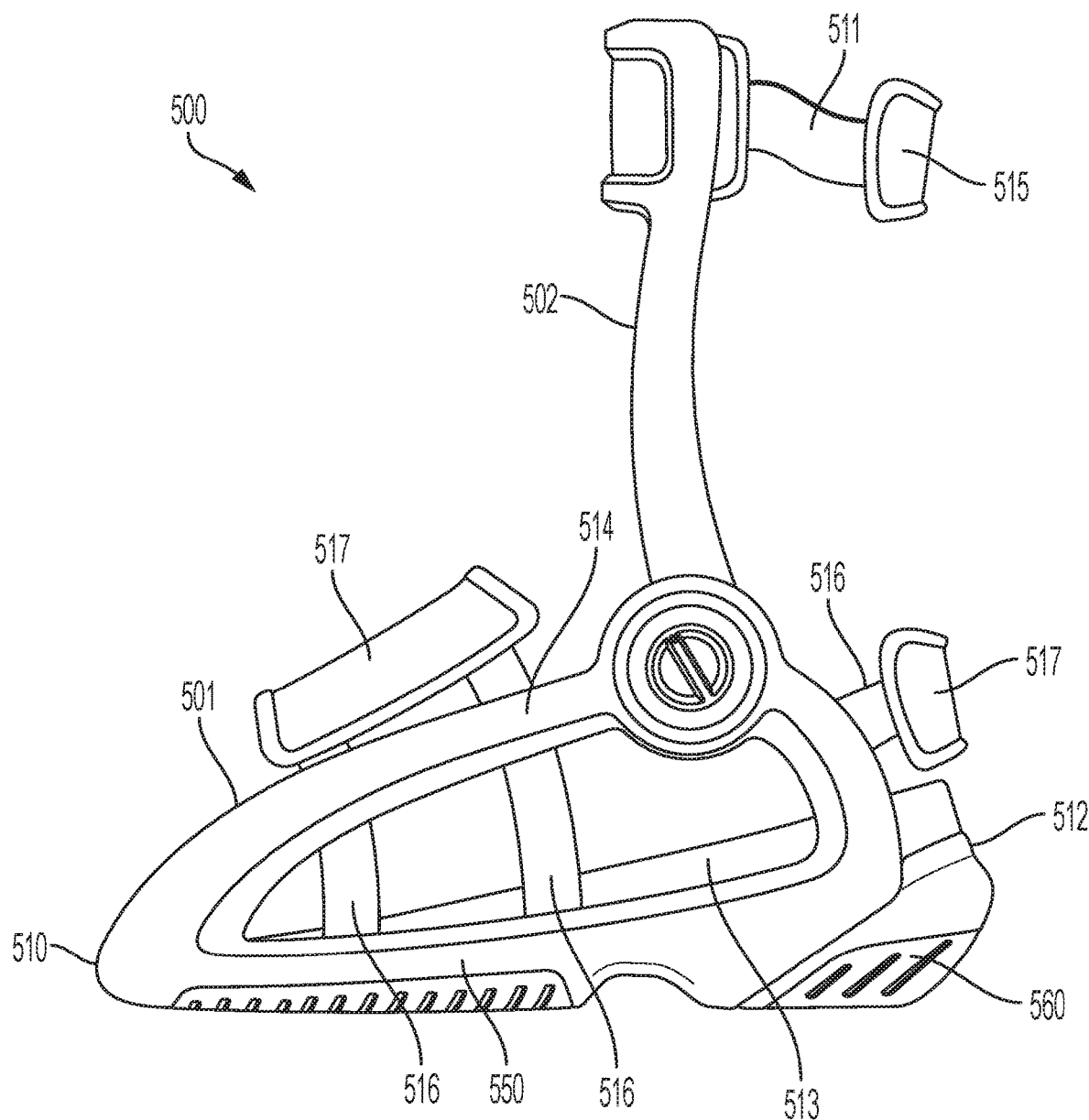
FIG. 20 is a left side view of the device of FIG. 19.

As shown in FIGS. 8A and 8B, for example, the device 100 may further comprise at least one strap 116 affixed to respective sides of the foot support portion 101 via, for example, slits 119 in each side of the framework 114. FIGS. 8-10 illustrate an embodiment with three straps 116, but it is contemplated that fewer or more straps may be used. As shown in FIGS. 8-10, the straps 116 may be configured to releasably secure the foot 121 of the user 123 to the foot support portion 101. The straps 116 can be adjustable to permit loosening and tightening of the straps around a user's foot. By way of example only, in various embodiments, the straps 116 may comprise hook and loop fasteners, such as, for example, Velcro®. As illustrated in the exemplary embodiment shown in FIGS. 17 and 18, in accordance with various exemplary embodiments, the exercise device 400 contemplates straps 416 each having a grip 417. The grips 417 may, for example, be positioned relative to the hook and loop fasteners on each of the straps 416, such that the user may grasp the grips 417 to open, close, and adjust the respective straps 416. Those of ordinary skill in the art will understand that the grips 417 may have various configurations, shapes, and/or features to help a user with opening, closing, and adjusting the straps 416. As illustrated in the embodiment of FIGS. 19 and 20, for example, the exercise device 500 includes enlarged, padded grips 517, which may be connected to multiple straps 516. In this manner, the grips 517 may function to both assist a user with opening, closing, and adjusting the straps 516, and to provide additional padding and support to the user's foot during use of the device 500. Those ordinarily skilled in the art will further understand that the straps 116, 416, 516 may comprise any type and/or configuration or mechanism to releasably secure a foot of the user to the foot support portion 101, 401, 501 including for example, snaps, buttons, ties, buckles, elastic bands, sliders, and/or any combination thereof.

To further prevent foot slippage and/or increase user comfort, the foot support surface 150 of the foot support portion 101 may also include various ridges, treads, coatings, applied surfaces, and/or other mechanisms to increase user comfort and/or to increase friction on the foot support surface 150 with which the foot comes into contact, for example, to massage the user's foot and/or prevent the foot from slipping on the foot support surface 150. Massage of the user's foot, via the foot support surface 150 and any elements, coatings, or surfaces applied thereto, will apply pressure to the sole of the foot during the exercise, i.e., plantar pressure, which also contributes to movement of fluid through the body tissue and to an increase in circulation of bodily fluids.

In accordance with various embodiments, the foot support surface 150 may also include various enhanced cushioning elements, such as, for example, elements that reduce shearing motions within the foot support surface 150, as described, for example, in U.S. Pat. No. 9,930,928 B2, entitled "Sole for a Shoe," the entire contents of which are incorporated by reference herein. As shown in FIGS. 1-10, the foot support surface may also include a removable pad 113 upon which the foot 121 may rest (see FIGS. 8A and 8B). The pad 113 may be made, for example, from a soft, form fitting material, such as, for example, a shape memory polymer, which may form to different users as well as promote hygiene as would be understood by those of ordinary skill in the art. Furthermore, as illustrated in the embodiments of FIGS. 17-20, exercise devices 400, 500, which include a foot support portion 401, 501 having a contoured foot support surface 450, 550 may include a contoured, removable pad 413, 513 (i.e., upon which the foot of the user may rest), which is configured to fit within the contoured boot of the device 400, 500.

Figure 7:
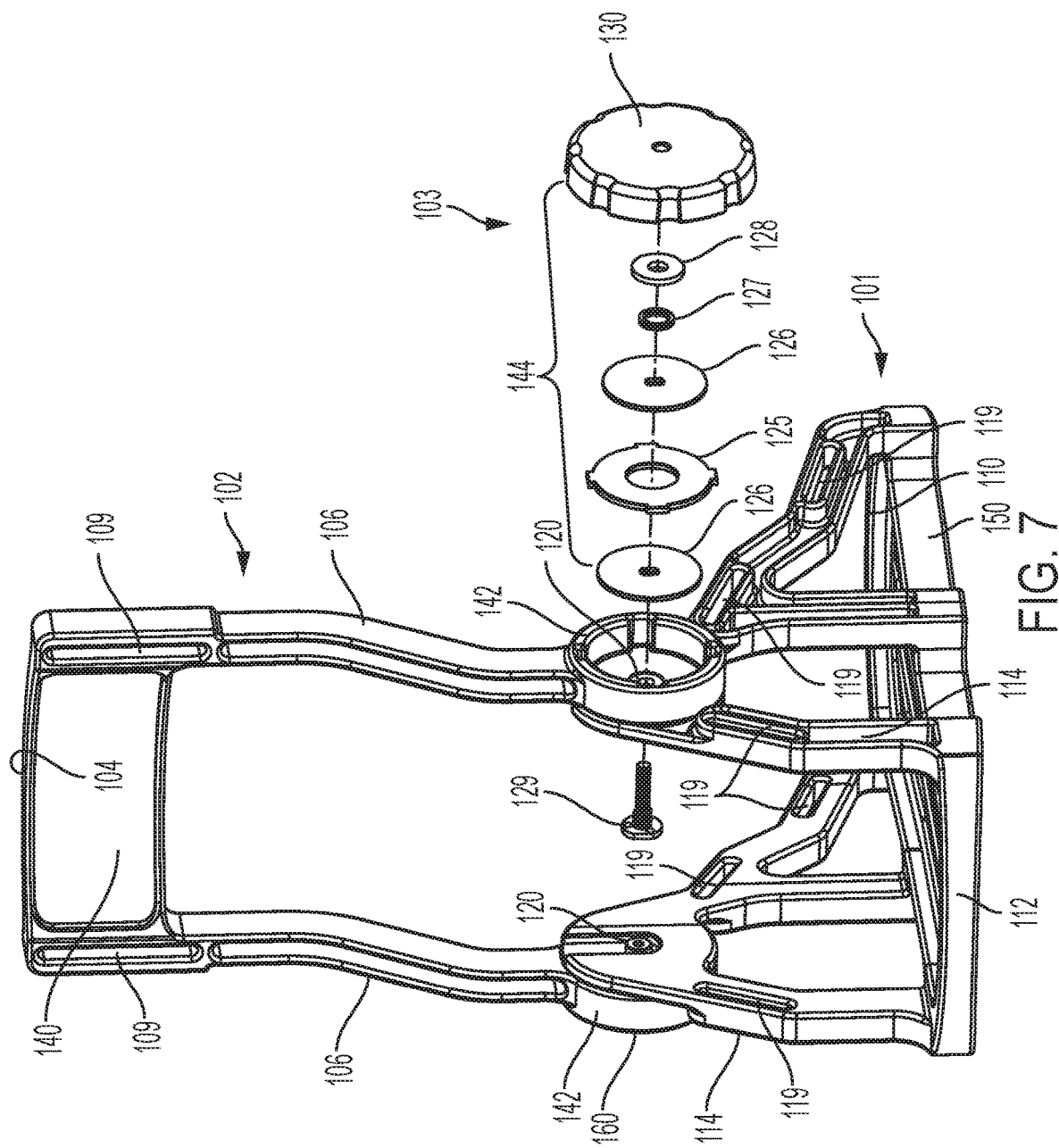
FIG. 7 is a perspective back view of the device of FIG. 1 showing an exploded view of a resistance mechanism in accordance with the present disclosure.

As illustrated in FIGS. 1-8, the foot support portion 101 is pivotably connected to the leg support portion 102 via a resistance mechanism 103. As best shown in the exploded view of FIG. 7, each leg 106 of the leg support portion 102 is configured to mate with a respective side of the framework 114 of the foot support portion 101 to form a hub 120 at which the device 100 pivots. As illustrated in FIG. 7, in accordance with one aspect of the present disclosure, each leg 106 may terminate in a housing 142 that is configured to encompass a respective hub 120. In such a configuration, a resistance mechanism 103 may be seated, for example, within one or both of the housings 142 to engage the respective hubs 120.

In various exemplary embodiments, the resistance mechanism 103 may comprise a friction device 144 configured to provide a frictional resistance to the rotational movement of the foot support portion 101 about the hubs 120. As shown in the exploded view of FIG. 7, in various exemplary embodiments, the friction device 144 may include an assembly of a tabbed drag washer 125 that is sandwiched between a pair of keyed drag washers 126 with a small amount of lubricant therebetween, a wave spring 127, and a spacer 128. In the orientation of FIG. 1-7, the assembly is stacked within the housing 142 located on a right side of the device 100, and a bolt 129 is inserted through both the hub 120 and the stacked assembly to engage an end cap 130. In this manner, the end cap 130 can be moved along the bolt 129 by applying a rotational motion to the end cap 130 (e.g., the user 123 can rotate the end cap 130 with their hand), which will in turn adjust the pressure on the stacked washers 125, 126 within the housing 142, while the housing 142 provides both lateral stability and a support surface for application of a transverse/compressive force. The wave spring 127 is configured to assist with modulation of the pressure applied to the stacked washers 125, 126, such that the rotation of the end cap 130 can be controlled to modify the pressure on the stacked washers 125, 126, and, thus, the degree of fiction created, with a level of resolution sufficient for clinical purposes.

With such a configuration, the foot support portion 101 is able to pivot toward and away from the leg support portion 102 and can have a neutral position N relative to a pivot axis P (see FIGS. 1 and 13). As used herein, the term "neutral position" refers to a foot support portion starting position and a position of the foot support portion 101 without external forces acting thereon to pivot the foot support portion 101 about the pivot axis P (e.g., about the hubs 120). Thus, as illustrated in FIG. 13, when the foot support portion 101 (not shown in the illustration of FIG. 13) is in the "neutral position," the leg 122 of a user, which is received by the leg support portion 102 (not shown in the illustration of FIG. 13), is in a relaxed, un-flexed position (i.e., the user's calf muscle is neither contracted nor stretched). In the exemplary embodiment of FIGS. 1-10, as best shown in FIGS. 9 and 10, in the "neutral position", the foot support portion 101 is positioned at approximately 90 degrees relative to the leg support portion 102. As will be described in further detail below with reference to FIGS. 8A and 8B, the foot support portion is configured to rotate about the pivot axis P in a first direction toward the leg support portion 102 and in a second direction away from the leg support portion 102. In this manner, as illustrated in FIG. 13, rotation is about an axis provided by the ankle 141 (i.e., the pivot axis P coincides with the natural pivot axis of the ankle 141), such that only the foot 121 moves around the axis P in the first and second directions and the leg 122 is stationary.

As will be understood by those of ordinary skill in the art, during the rotation of the foot support portion 101, the friction device 144 exerts a force on the foot support portion 101 about the pivot axis P opposite to the respective first and second directions of rotation of the foot support portion 101 about the pivot axis P. For example, the friction force created by the stacked washers 125, 126 may provide a passive resistance to the rotational movement of the foot support portion 101 throughout a full range of ankle flexion and extension of the foot 121. In other words, the friction force created by the stacked washers 125, 126 (which resists the rotation of the foot support portion 101) is constant throughout all movements of the foot support portion 101 (i.e., the force exerted against the rotation of the foot support portion 101 as it moves away from the neutral position is the same as the force exerted against the rotation of the foot support portion 101 as it moves back to the neutral position). As will be further understood by those of ordinary skill in the art, during the rotation of the foot support portion 101, in various additional embodiments, the friction device 144 also exerts a force on the foot support portion 101 that is proportional to a velocity of user input. In other words, the friction force created by the stacked washers 125, 126 (which resists the rotation of the foot support portion 101) is proportional to the velocity of the rotational movement of the foot support portion 101 with respect to the neutral position, as applied by the user of the device 100.

Those of ordinary skill in the art will understand, however, that resistance mechanisms in accordance with the present disclosure may comprise various types, numbers, configurations, and/or combinations of mechanisms that may exert a force on the foot support portion 101 about the pivot axis P opposite to the respective first and second directions of rotation of the foot support portion 101 and are not limited in any way to friction devices, or to the particular exemplary friction device 124 of the embodiment illustrated in FIGS. 1-10. Examples of such resistance mechanisms other than friction devices that can be used, or that can be used in combination with friction devices, include but are not limited to, torsion bars, spring devices (e.g., torsion springs/linear springs), detent dials, adjustable clutch mechanisms, piezoelectric/nanomotion motors, pneumatic, and/or hydraulic devices, such as, for example, hydraulic cylinders (see below), viscous damping devices, and/or devices utilizing smart fluids, such as, for example, magnetorheological fluids or electrorheological fluids.

Those of ordinary skill in the art will further understand that such resistance mechanisms may utilize a wide range of dynamics to provide the required resistance. For example, with reference to viscous damping devices, such devices may include, but are not limited to: (1) a non-compressible fluid (liquid or gas) that drives a rigid or elastomeric container/housing to move; (2) a non-compressible fluid that moves when put under pressure; (3) a compressible fluid that becomes more viscous as it is compressed; and/or (4) a compressible fluid that moves.

Various additional embodiments of the present disclosure contemplate, for example, adding a torsion spring (not shown) to the stacked assembly of the friction device 144 to provide a bi-directional, increasing resistance during rotation of the foot support portion 101. In other words, with the addition of a torsion spring, as the torsion spring is rotated about the pivot axis P (via the foot support portion 101), the torsion spring may store a torque T (i.e., the stored torque T is substantially equal to the amount of torque placed upon the torsion spring), so that when the torque is removed from the torsion spring the foot support portion 101 is assisted by the torsion spring in returning to its starting position (i.e., the neutral position). In this manner, the torsion spring is configured to exert a stored torque T on the foot support portion 101 opposite to the direction of rotation (toward or away from the leg support portion 102) of the foot support portion 101 about the pivot axis P, and the amount of stored torque T (counteracting torque) exerted by the torsion spring on the foot support portion 101 is proportional to the amount by which the foot support portion 101 is rotated about the pivot axis P and away from the neutral position.

Accordingly, in various exemplary embodiments of the present disclosure, the torque exerted by the torsion spring may provide passive resistance to rotational movement of the foot support portion 101 in both directions about the pivot axis P, and an amount of the torque may vary with a degree of rotation θ (see FIGS. 8A and 8B) of the foot support portion 101 about the pivot axis P, for example, the amount of torque may increase with the degree of rotation θ of the foot support portion 101 about the pivot axis P.

Various further embodiments of the present disclosure also contemplate that the device 100 may include an electric motor (not shown) that is configured to assist with the rotational movement of the foot support portion 101. The electric motor may, for example, be utilized by users with little or no muscle strength to assist with rotating the foot support portion 101 and/or to maintain/improve a user's range of motion while using the device 100. Additional embodiments further contemplate a resistance mechanism 103 that includes a spring mechanism (not shown) configured to assist with returning the foot support portion 101 to the neutral position. Such a spring mechanism may be either included within the resistance mechanism 103 or may be a separate mechanism that is configured to be engaged/disengaged to assist with returning the foot support portion 101 to the neutral position. Those of ordinary skill in the art will further understand that various types and/or configurations of mechanisms may be used to increase a user's range of motion while using the device 100 and/or assist with returning the foot support portion 101 to the neutral position.

To accommodate users in various positions, the device 100 may be used in both a sitting position and a supine position. For example, as will be understood by those of ordinary skill in the art, the positioning of the device 100 can be adjusted such that the foot support portion 101 is disposed in a first position wherein the foot support portion 101 is in the neutral position to receive a foot 121 of a user 123 in a sitting position (see FIG. 9) and a second position wherein the foot support portion 101 is in the neutral position to receive a foot 121 of a user 123 in a supine position (see FIG. 10). In one example, to better support use in the supine position, the heel end portion 112 of the foot support portion 101 may include a rocker (not shown) configured to allow the foot support portion 101 to rock back and forth along the surface supporting the device 100 (e.g., a bed surface 170) as the foot support portion 101 rotates about the pivot axis P.

In various exemplary embodiments of the present disclosure, to further accommodate a broad range of users, including, for example, travelers, the device 100 may also have a portable configuration. In the portable configuration, for example, the leg support portion 102 may rotate into alignment with the foot support portion 101, thereby folding the leg support portion 102 against the foot support portion 101 to make the device 100 more compact for transportation or storage. One or more of the straps 111, 116 may also be used to secure the leg support portion 102 to the foot support portion 101 to maintain the device 100 in the portable configuration. Those ordinarily skilled in the art will understand, however, that the leg support portion 102 and/or foot support portion 101 may comprise any type and/or configuration of mechanism to releasably secure the leg support portion 102 to the foot support portion 101. Furthermore, in the portable configuration, the contoured plate 104 and/or portions of the framework 114 can serve as a handle to carry the device 100.

Various additional exemplary embodiments of the present disclose further contemplate a portable configuration in which portions of the framework 114 may be configured such that the framework 114 may collapse down onto the foot support surface 150 of the foot support portion 101, such that the foot support portion 101 may generally pack flat. And, various further exemplary embodiments of the present disclosure contemplate a portable configuration in which both the foot support portion 101 and the leg support portion 102 are inflatable, such that the device 100 may be deflated to become more compact for transportation and storage.

Figure 4:
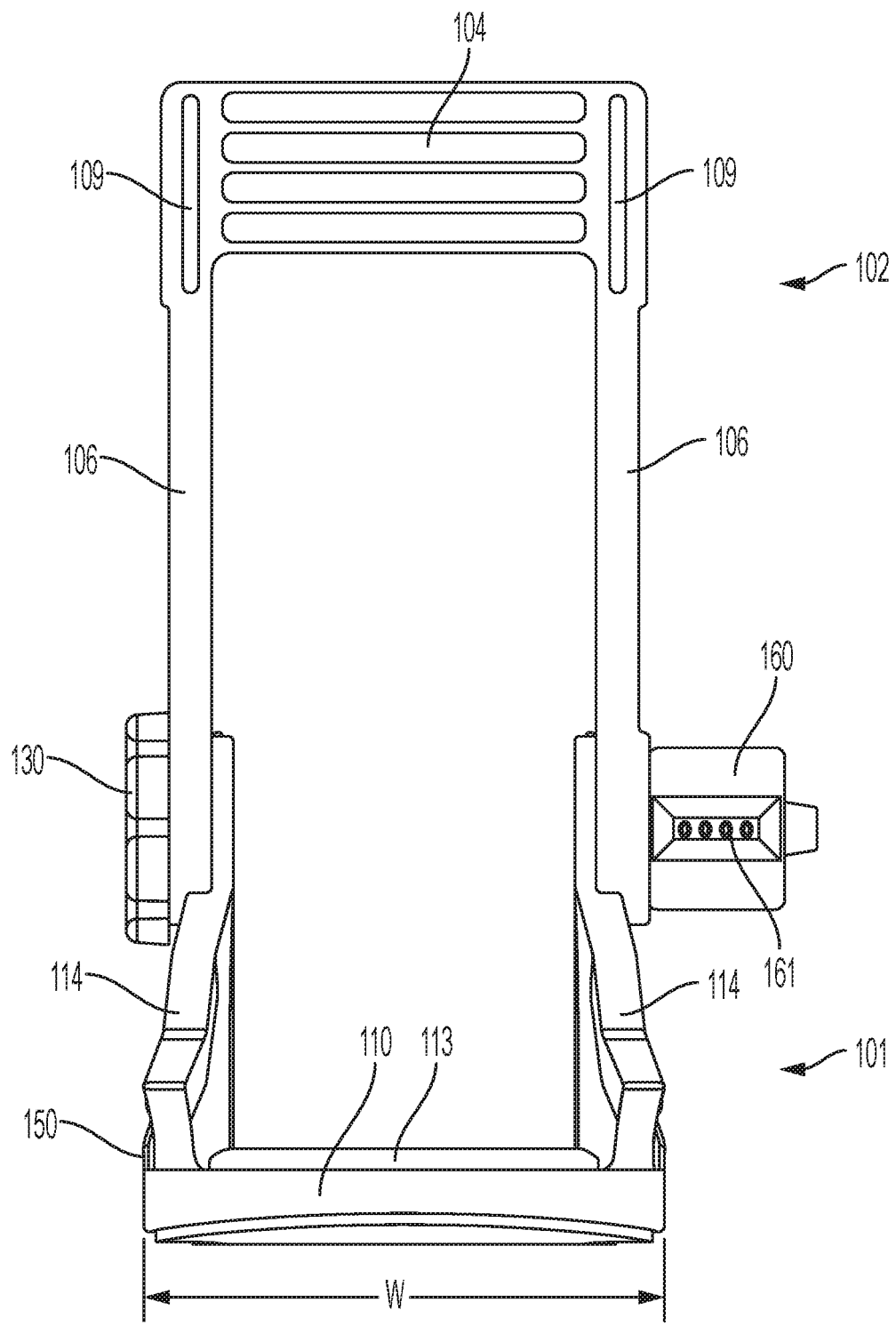
FIG. 4 is a front view of the device of FIG. 1.
Figure 5:
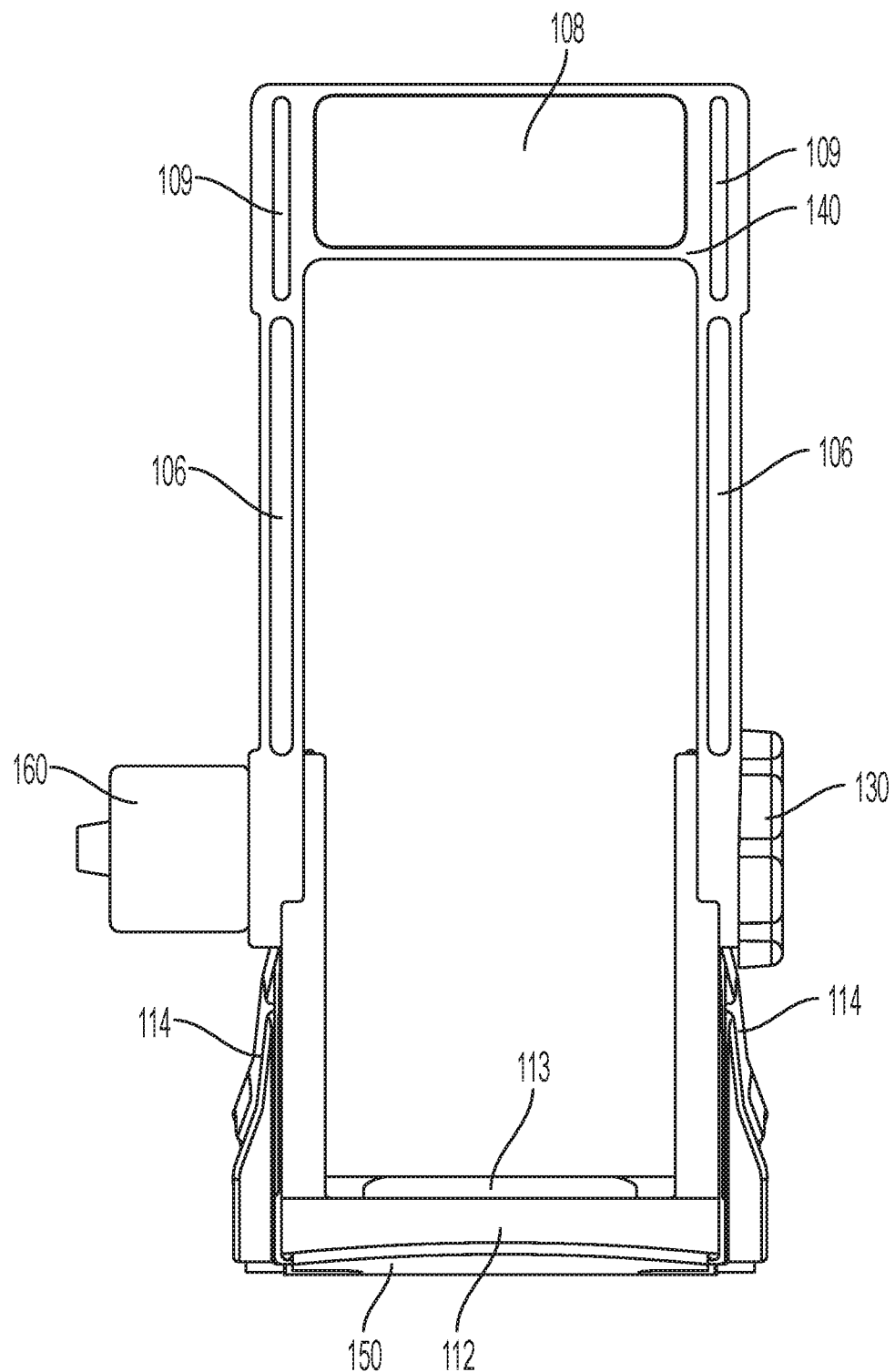
FIG. 5 is a back view of the device of FIG. 1.
Figure 6:
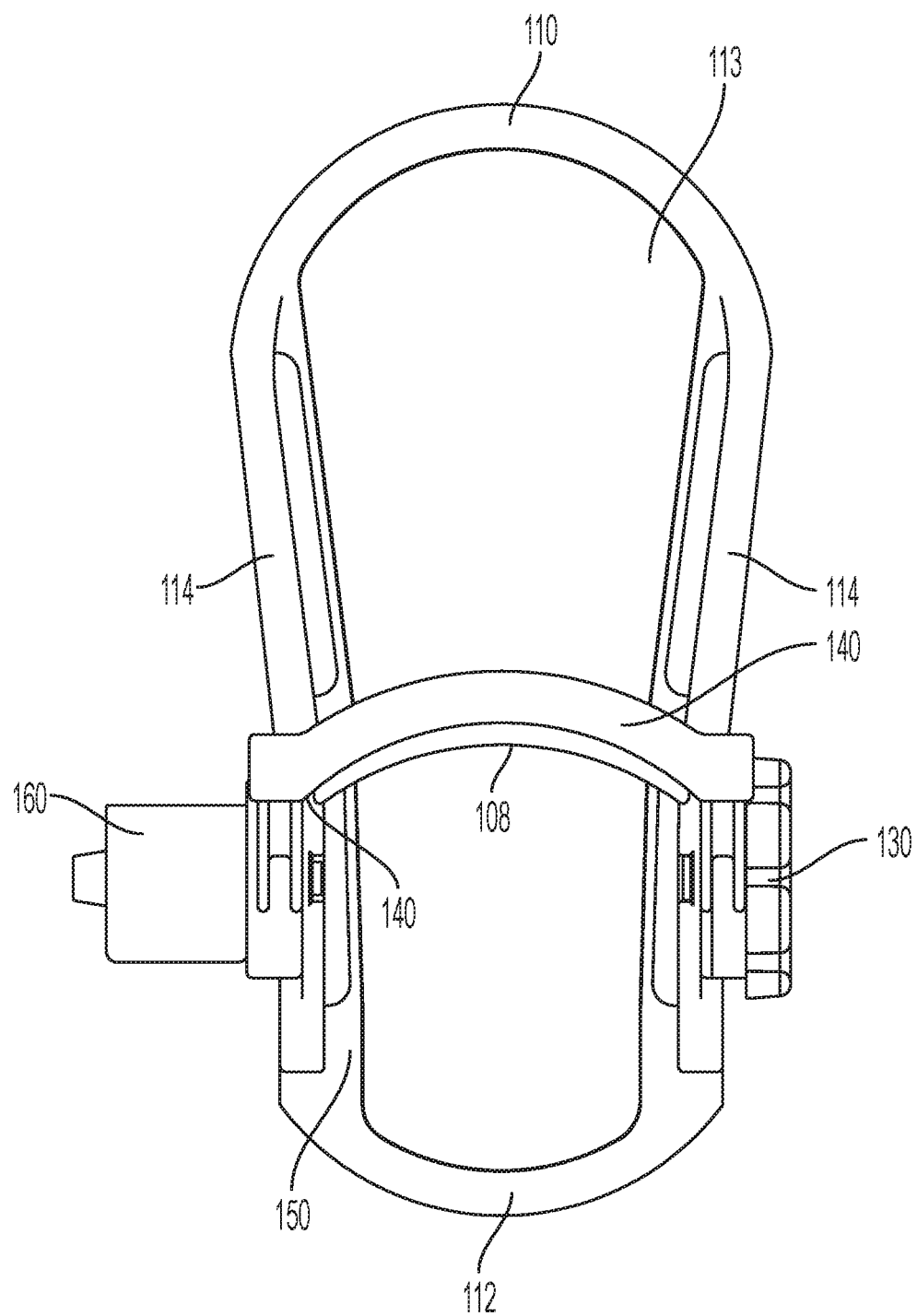
FIG. 6 is a top view of the device of FIG. 1.

To aid with compliance monitoring and goal tracking, as best illustrated perhaps in FIGS. 1 and 4, various exemplary embodiments of the present disclosure may also include a compliance monitoring device 160 that is configured, for example, to count and show on a display 161 a number of repetitions made by the foot support portion 101. As used herein the term "repetition" refers to one complete motion of an exercise. For example, a repetition may include the complete movement of the foot support portion 101 in both the first and second directions away from the neutral position, or to a number of rotations made by the foot support portion 101 about the pivot axis P. Similar to the resistance mechanism 103, for example, the compliance monitoring device 160 may be configured such that it may sit within one of the housings 142 of the leg support portion 102 to engage a respective hub 120 of the device 100. As illustrated in FIGS. 1 and 4, for example, in various exemplary embodiments, a conventional tally type counter may be used and seated within one of the housings 142 to track and show on an analog display 161 the number of times the hub 120 rotates about the pivot axis P. Those of ordinary skill in the art will understand, however, that the compliance monitoring device 160 may include various types, configurations, and/or numbers of devices both analog and digital to track and display the number of repetitions of the foot support portion 101, and may further include various additional tracking devices, both analog and digital, such as, for example, clocks, timers, gauges, and/or sensors, to aid in compliance monitoring and goal tracking. In various additional embodiments, for example, the compliance monitoring device 160 may be further configured to track a degree of rotation of the foot support portion 101 (i.e., away from the pivot axis P) in each direction and/or an amount of force applied to the foot support portion 101 during its rotation. In other words, the compliance monitoring device may track and record the distance traveled by the foot support portion 101 (i.e., with respect to the neutral position N) and/or the force applied by the user to the foot support portion 101 during each repetition. In this manner, the compliance monitoring device 160 may monitor a user's progress, for example, by comparing the output of various repetitions. Furthermore, such monitoring devices may be configured to wirelessly transmit tracking data to a display, such as, for example, a user's television, computer, tablet, smart phone, or other display, as those of ordinary skill in the art will understand. Those of ordinary skill in the art will further understand that the measurements taken by the device 160 may be taken in various forms, such as, for example, in terms of work, power output, and/or impulse (i.e., force over time).

Various additional exemplary embodiments of the present disclosure may further include a variety of additional monitoring and/or sensing devices that may, for example, track a user's (i.e., patient's) vitals and/or electrically monitor a user's muscle activity (e.g., electroencephalogram (EEG) and/or electromyography (EMG)). For example, in accordance with various embodiments, the foot support portion 101 and/or leg support portion 102 may include a pulse oximeter, blood pressure monitor, a temperature sensor, and/or various surface electrodes, and may further include a data storage device that can both store and transmit data related, for example, to the user's blood oxygen level, heart rate, blood pressure, temperature, and/or muscle activity. The data storage device, for example, may be readable by a processing system, and include both volatile and nonvolatile media, removable and non-removable media, and contemplates media readable by a database, a computer, and various other network devices. Various embodiments of the present disclosure contemplate, for example, plugging a USB cable or other data transfer cable into a port on the device that interfaces with the data storage device to transfer stored information to a computer or other remote device.

Various additional embodiments of the present disclosure may, for example, also include telemetric monitoring devices, which incorporate various known wireless information system technologies that can collect and transmit both patient vital data and environmental data remotely. Such telemetric devices may include, for example, computers that weave on-body sensors into the foot support portion 101 and/or leg support portion 102 and transmit data remotely to, for example, handheld devices, such as mobile phones, tablets, and personal digital assistants, smart watches, nursing stations, and/or doctor's offices. Furthermore, such telemetric devices can be configured to transmit data to a chosen remote location automatically, such as, for example at scheduled intervals, daily, or weekly.

As one ordinarily skilled in the art will understand, exercise devices in accordance with the present disclosure may include various additional features and may be used in conjunction with various additional medical and/or physical therapy devices. Various further embodiments may include, for example, a temperature regulation device, such as for example, a thermoelectric cooler and/or a heater (e.g., chemo-generated or via a battery pack); an electrical stimulation device (e.g., which may stimulate blood flow, reduce soft tissue inflammation, and/or facilitate muscle contraction, such as assisting gate in MS patients); a sequential compression device (SCD) (e.g., which may be used to reduce venous stasis and deep venous thrombosis after, for example, joint replacement); and/or a device that provides range of motion assist (e.g., a device that takes the range of motion of the foot support portion 101 beyond the limits that the patient is reaching). As one of ordinary skill in the art will further understand, such features and devices may, for example, be incorporated within the exercise device itself, or may be a separate component that is used in conjunction with the exercise device.

Figure 14:
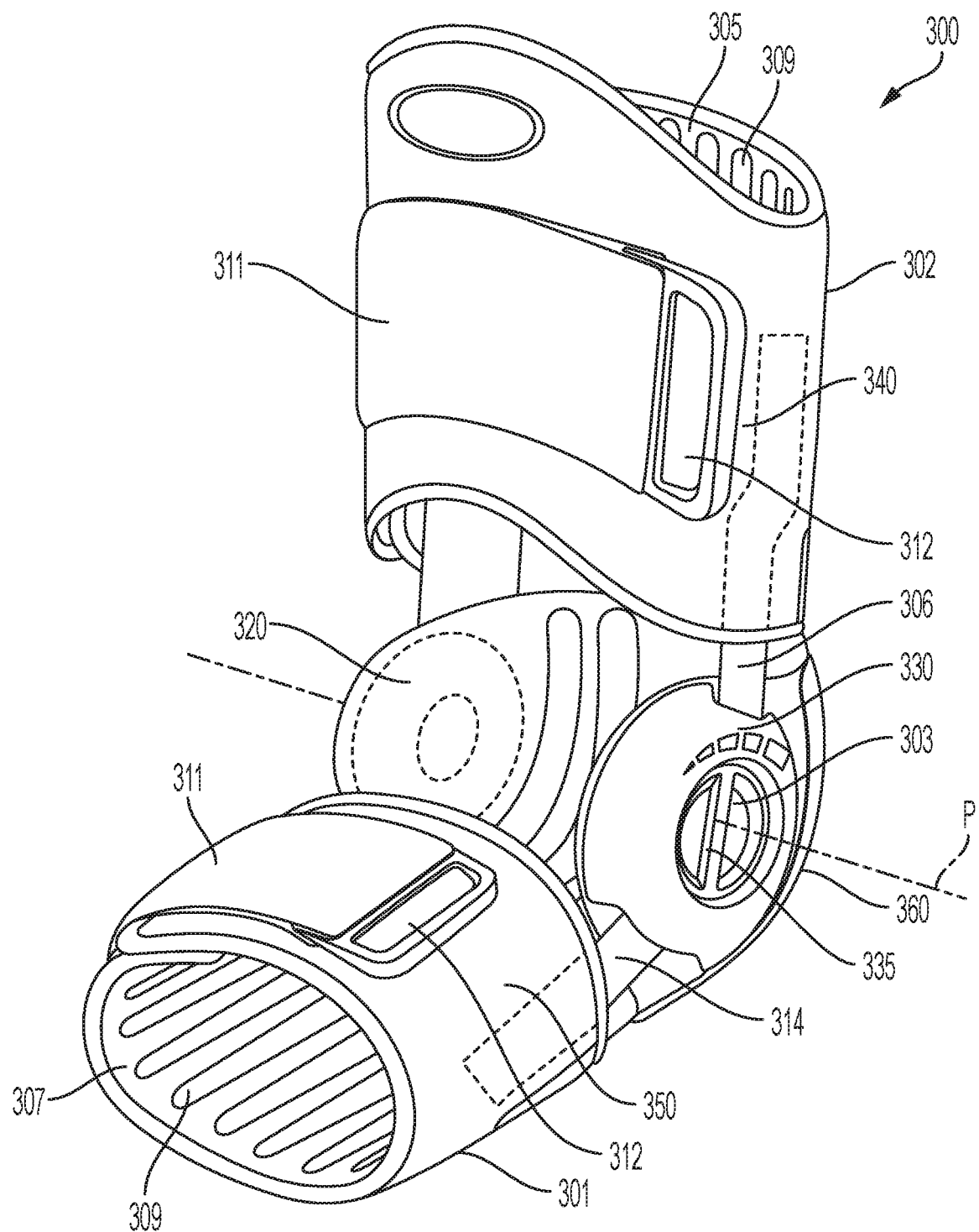
FIG. 14 is a perspective, front left side view of another exemplary embodiment of an exercise device in a closed configuration in accordance with the present disclosure.
Figure 15:
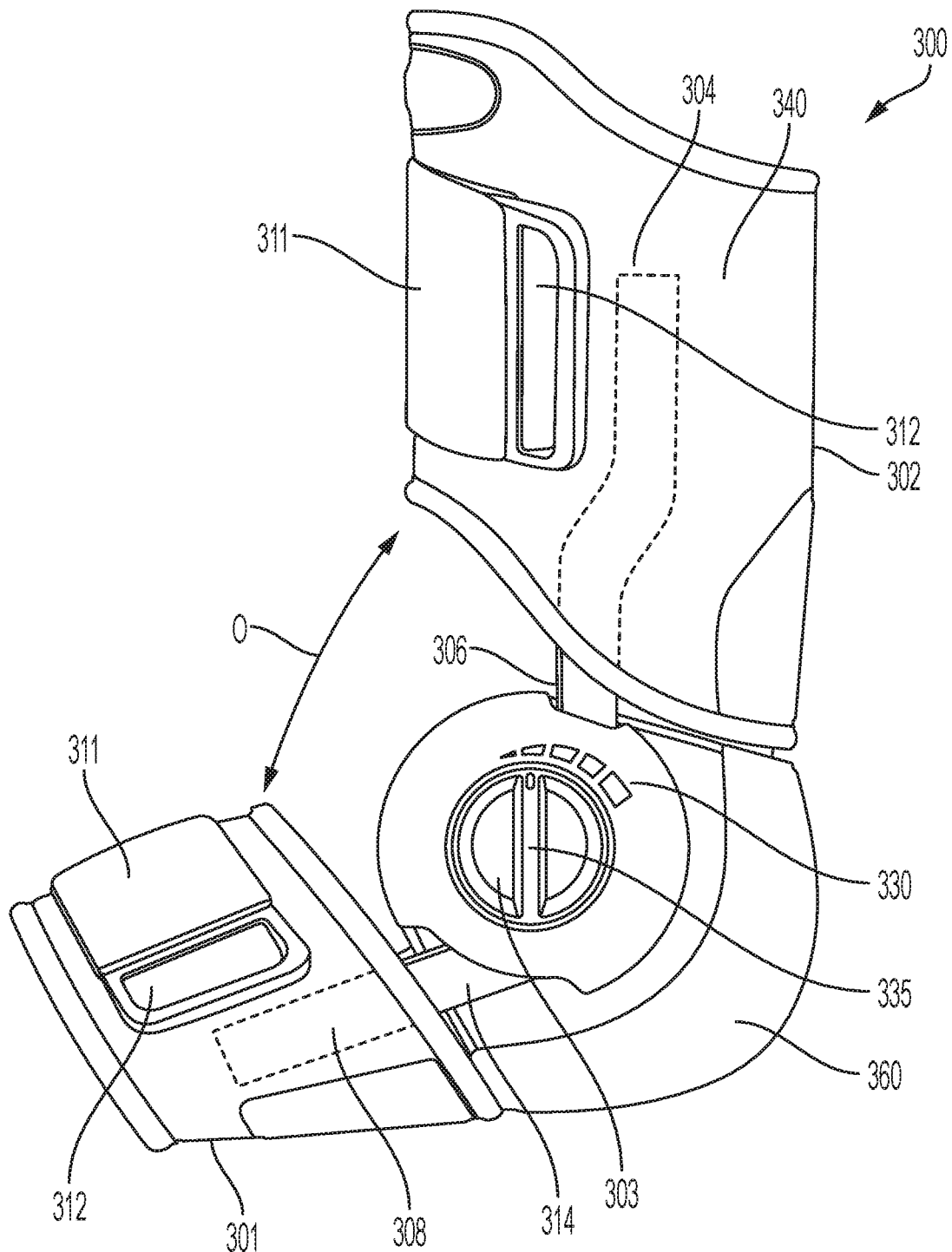
FIG. 15 is a left side view of the device of FIG. 14 in the closed configuration.
Figure 16:
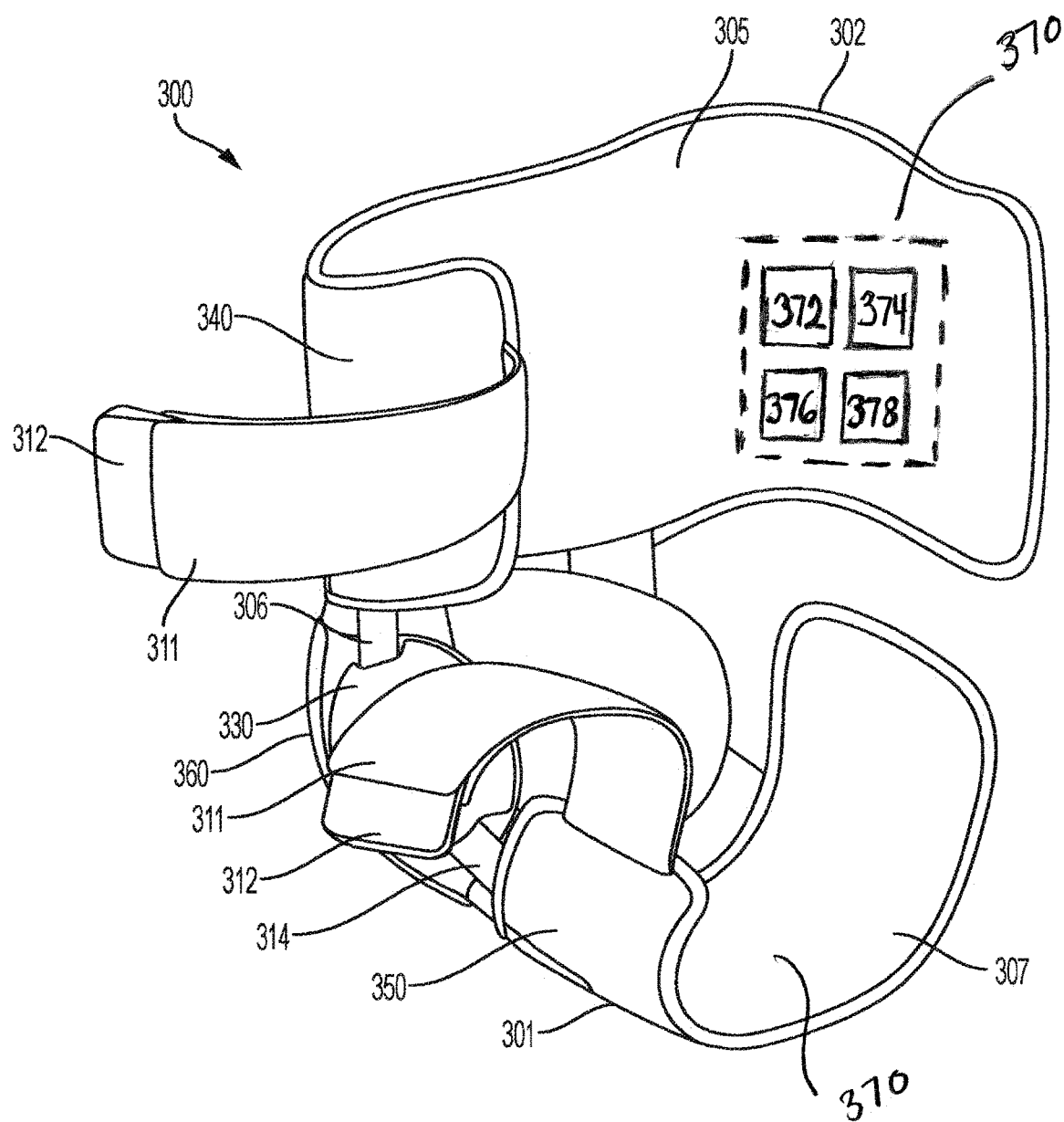
FIG. 16 is a perspective, front right side view of the device of FIG. 14 in an open configuration.
Figure 17:
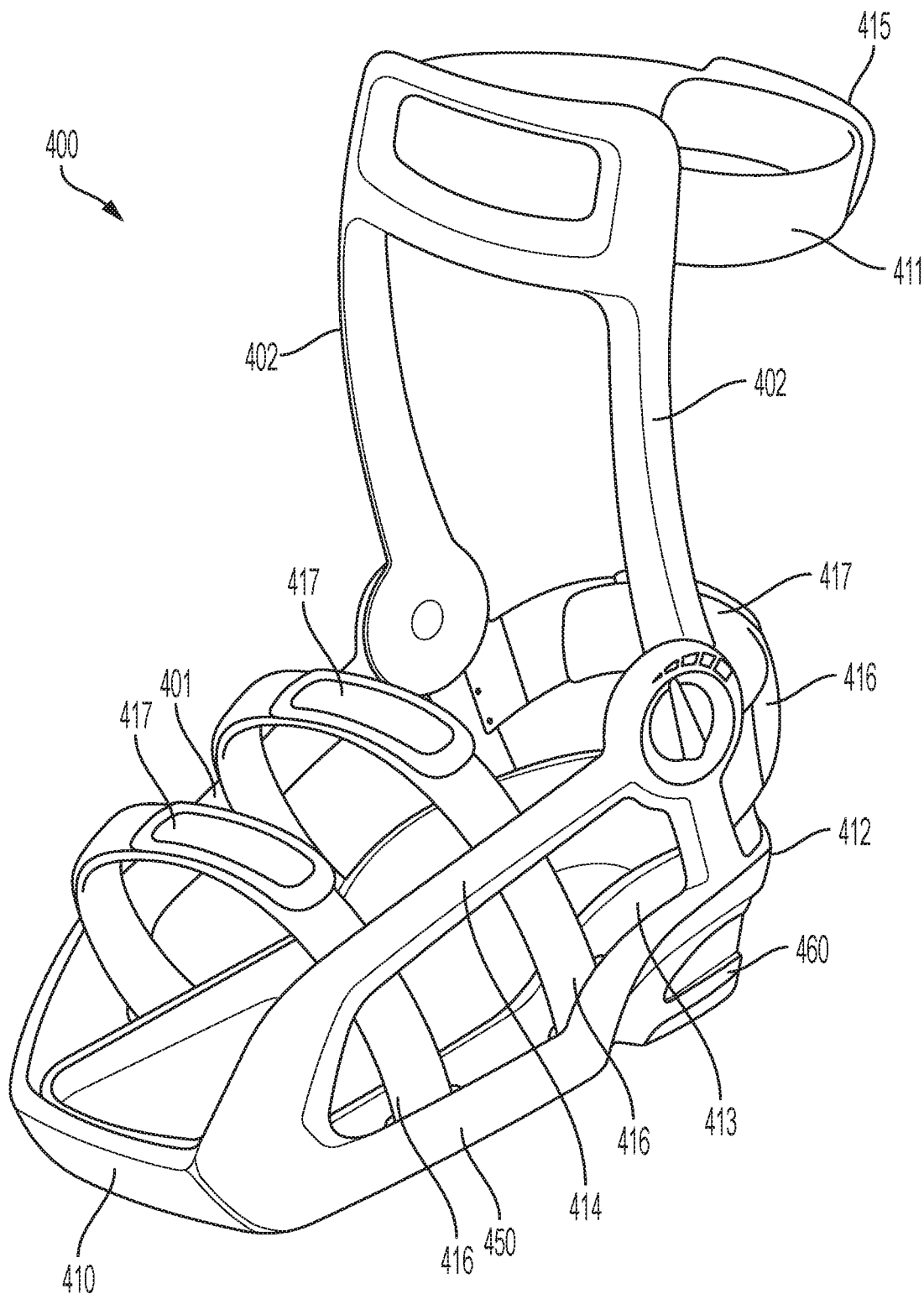
FIG. 17 is a perspective, front left side view of another exemplary embodiment of an exercise device in accordance with the present disclosure.
Figure 18:
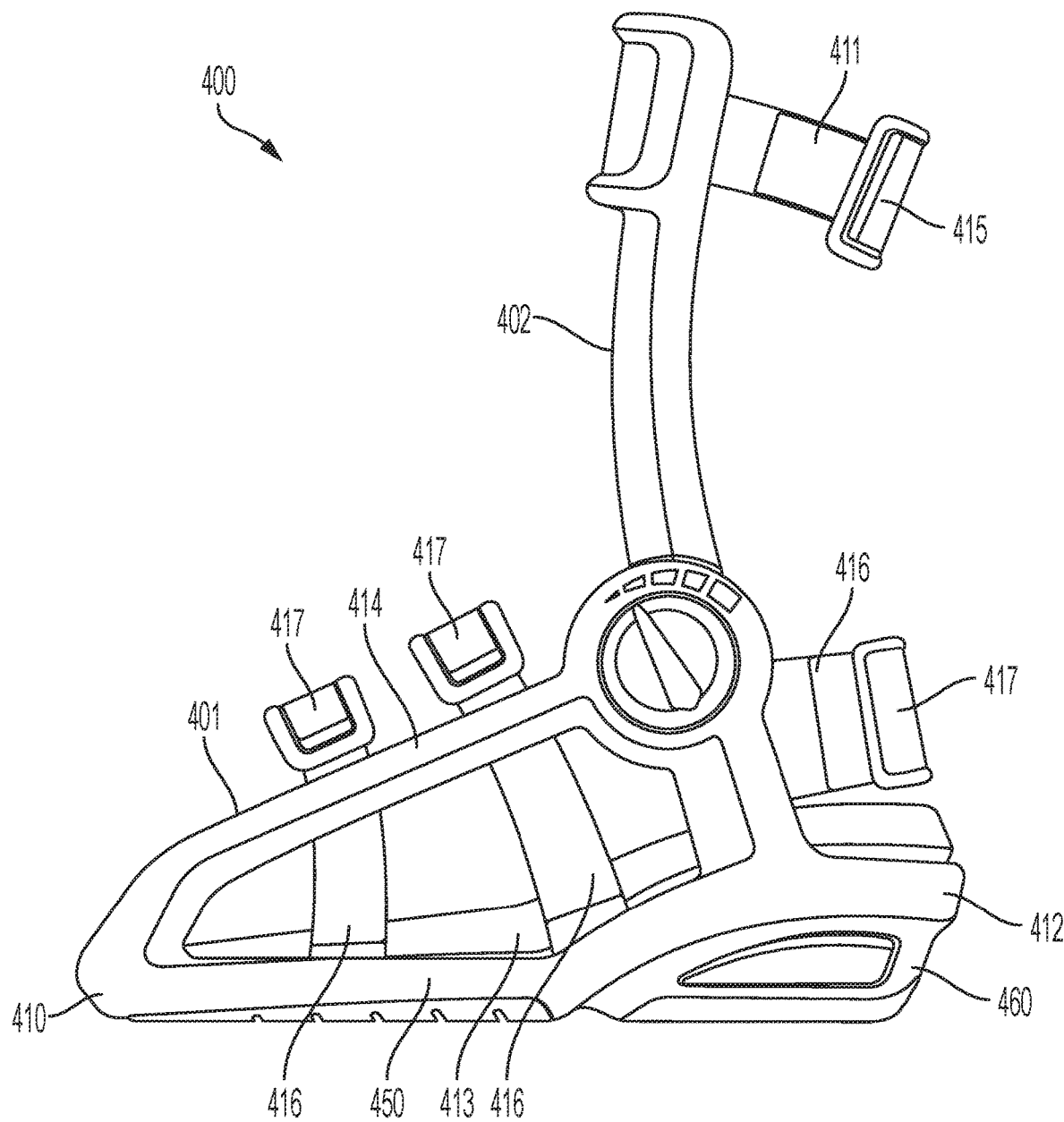
FIG. 18 is a left side view of the device of FIG. 17.

As an example, various embodiments of the present disclosure contemplate incorporating the components of a SCD device directly into the framework of the device 100 or into the material of a soft goods version of the device (e.g., within the material of the device 300 illustrated in FIGS. 14-16). An example of appropriate structure to be incorporated from a SCD device is described, for example, in International Patent Application Publication No. WO 2015196190 A1, entitled "Intermittent and Sequential Compression Device and Method," the entire contents of which are incorporated by reference herein. Various embodiments of the present disclosure further contemplate incorporating the components of a VenaFlow® System, which combines rapid inflation and graduated sequential compression to accelerate venous velocity and enhance fibrinolysis, within the material of the device. In such an embodiment, the air pockets of the SCD device may, for example, be incorporated directly into the respective devices (100, 200, 300, 400, 500). Such embodiments may further include a pressure control mechanism, which may either automatically or manually (i.e., via a user control) be used to increase/decrease the pressure exerted by the air pockets. In this manner, devices in accordance with the present disclosure may provide a complete therapy package, allowing a user to wear the device for extended periods of time and even sleep with the device on, while appropriately switching between therapeutic/prophylactic measures (i.e., exercise and compression).

As another example, various embodiments of the present disclosure contemplate incorporating heated insoles and/or employing a heating element within the device itself. An exemplary heated insole is described, for example, in International Patent Application No. WO 2013101920 A1, entitled "Heated Insoles of Shoes," the entire contents of which are incorporated by reference herein. An exemplary heating element for incorporation into the devices made in accordance with the present disclosure is shown in U.S. Pat. No. 5,041,717, entitled "Universal Ski Boot Heater," the entire contents of which are incorporated by reference herein.

Figure 11:
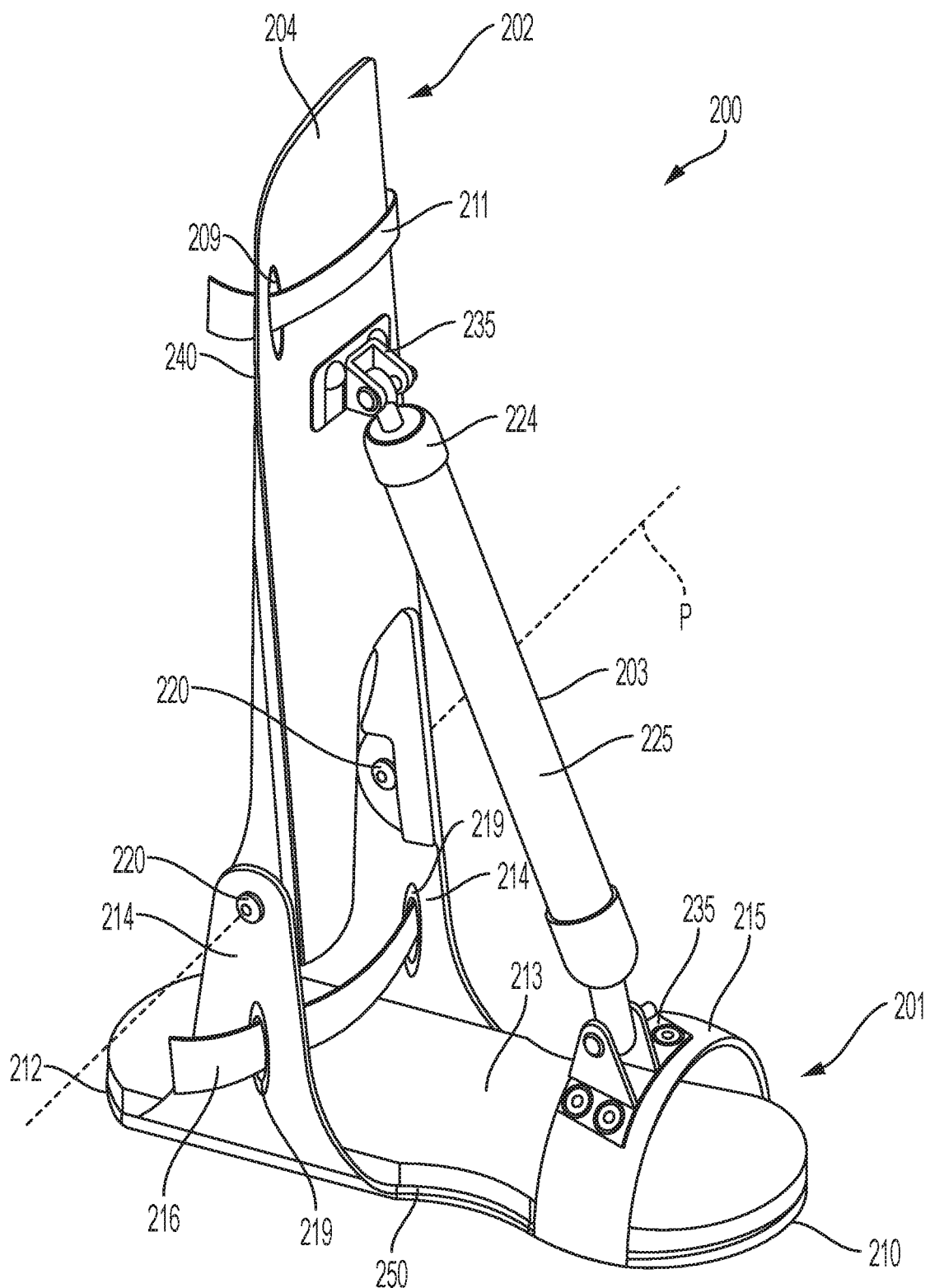
FIG. 11 is a perspective front view of another exemplary embodiment of an exercise device in accordance with the present disclosure.
Figure 12:
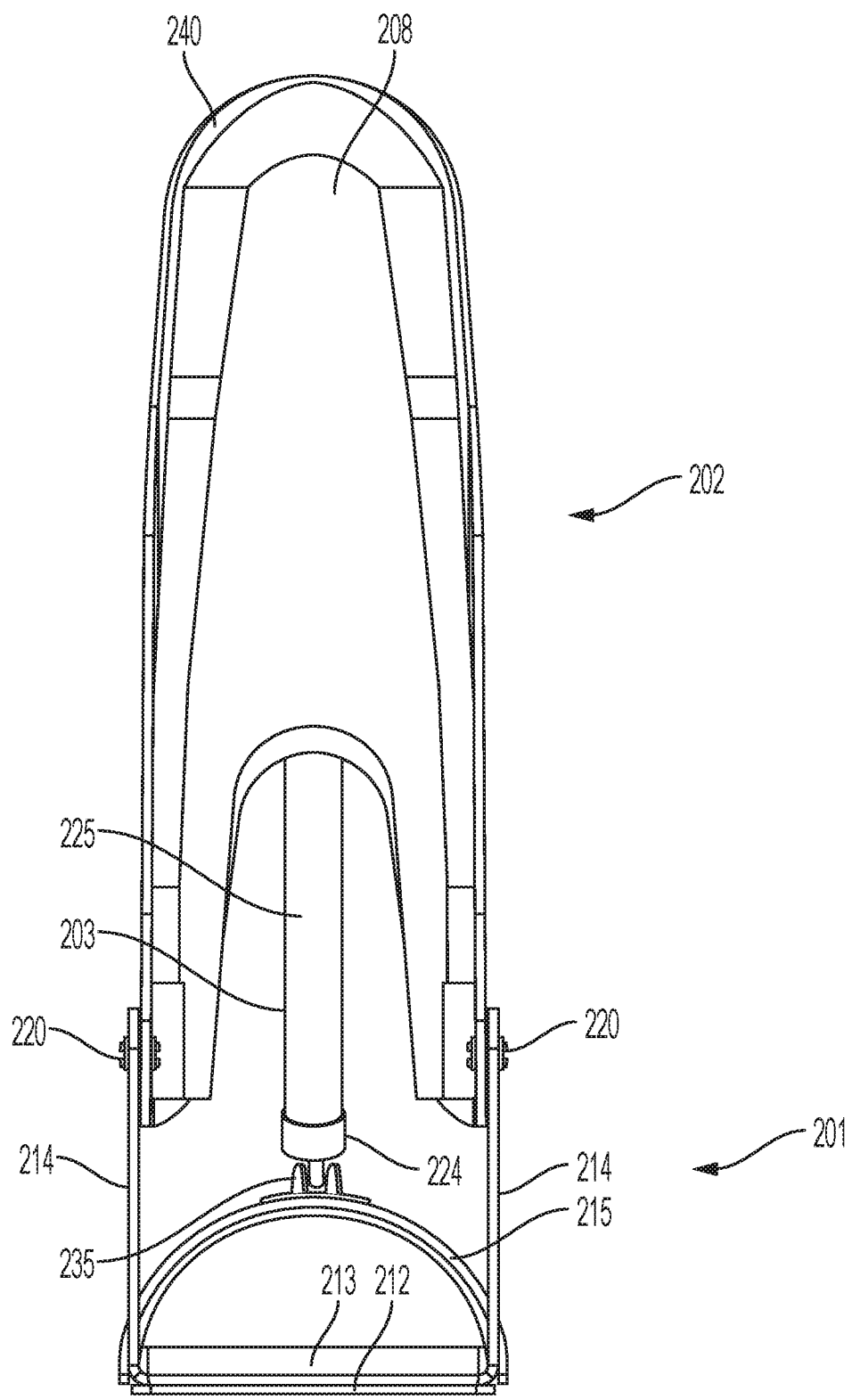
FIG. 12 is a back view of the device of FIG. 11.

FIGS. 11 and 12 illustrate an exemplary exercise device 200 in accordance with another exemplary embodiment of the present disclosure. As shown in FIGS. 11 and 12, the exercise device 200 includes a leg support portion 202, a foot support portion 201, and a resistance mechanism 203. Similar to the embodiment of FIGS. 1-10, the foot support portion 201 extends from an end of the leg support portion 202 and is pivotably connected relative to the leg support portion 202. Also similar to the embodiment of FIGS. 1-10, the leg support portion 202 provides a leg support surface 240 configured to receive and support a leg of a user while the user is using the device 200, and the foot support portion 201 provides a foot support surface 250 configured to receive and support a foot of the user while the user is using the device 200.

As above, the leg support portion 202 includes a contoured plate 204 provided with a leg support surface 240 that is configured to receive a leg of a user. Also as above, the contoured plate 204 is configured to connect to the foot support portion 201 at a pivot axis P. As perhaps best shown in FIG. 12, to more comfortably accommodate various users, the leg support surface 240 of the contoured plate 204 includes a depression 208 that is removably mountable to the plate 204 and comes in multiple sizes. In various exemplary embodiments, for example, the depression 208 may be made from a soft, form fitting material, such as, for example, a shape memory polymer, which may form to different users as well as promote hygiene as would be understood by those of ordinary skill in the art.

As illustrated in FIG. 11, in various exemplary embodiments, the leg support portion 202 may further comprise at least one strap 211 affixed to respective sides of the leg support portion 202 via, for example, slits 209 in each side of the contoured plate 204. The strap 211 may, for example, be configured to releasably secure around the leg of the user to assist in securing the device 200 to the leg. By way of example only, in various embodiments, the strap 211 may comprise hook and loop fasteners, such as, for example, Velcro®. Those ordinarily skilled in the art will further understand that the strap 211 may comprise any type and/or configuration of mechanism to releasably secure the leg of the user to the leg support portion 202, including for example, cuffs, snaps, buttons, ties, buckles, elastic bands and/or any combination thereof.

As above, those ordinarily skilled in the art will further understand that the leg support portion 202 may have various sizes, shapes, configurations and/or features without departing from the scope of the present disclosure.

In the orientation of FIGS. 11 and 12, the foot support portion 201 includes a foot support surface 250, having a toe end portion 210 and a heel end portion 212, and a pair of arms 214 that extend upwardly from the foot support surface 250 to connect the foot support portion 201 to the leg support portion 202. The foot support portion 201 further includes a band 215 that is positioned adjacent to the toe end portion 210 of the foot support surface 250, and which is configured to receive the toes of the user's foot. Thus, as illustrated in FIGS. 11 and 12, the foot support portion 201 of the device 200 is generally shaped like a slipper or sandal. As above, those ordinarily skilled in the art will understand, however, that the foot support portion 201 may have various sizes, shapes, configurations and/or features without departing from the scope of the present disclosure.

In various exemplary embodiments, for example, the foot support portion 201 may further comprise a strap 216 affixed to and extending between the arms 214 of the foot support portion 201 via, for example, slits 219 in each of the arms 214. The strap 216 may be configured to releasably secure the foot of the user to the foot support portion 201. For example, the strap 216 can be adjustable to permit loosening and tightening of the strap 216 around a user's ankle. By way of example only, in various embodiments, the strap 216 may comprise hook and loop fasteners, such as, for example, Velcro®. Those ordinarily skilled in the art will further understand that the strap 216 may comprise any type and/or configuration or mechanism to releasably secure a foot of the user to the foot support portion 201, including for example, snaps, buttons, ties, buckles, elastic bands and/or any combination thereof.

As above, to further prevent foot slippage and/or increase user comfort, in various additional exemplary embodiments, the foot support surface 250 of the foot support portion 201 may also include various ridges, treads, coatings, applied surfaces, and/or other mechanisms to increase user comfort and/or to increase friction on the foot support surface 250 with which the foot comes into contact, for example, to massage the user's foot and/or prevent the foot from slipping on the foot support surface 250. Similar to the exemplary embodiment of FIGS. 1-10, in various exemplary embodiments the foot support surface 250 may include a removable pad 213 upon which the foot may rest. In various embodiments, for example, the pad 213 may be made from a soft, form fitting material, such as, for example, a shape memory polymer, which may form to different users as well as promote hygiene as would be understood by those of ordinary skill in the art.

As illustrated in FIGS. 11 and 12, the foot support portion 201 is pivotably connected to the leg support portion 202 via pivots, which as shown in the exemplary embodiment of FIGS. 11 and 12, may include, for example, a pair of bolts 220. As those of ordinary skill in the art will understand, however, the disclosed pivots may include various numbers, types and/or configurations of mechanisms, which allow the foot support portion 201 to rotate with respect to the leg support portion about the pivot axis P. The leg support portion 202 is configured to be positioned between and connected to each of the arms 214 of the foot support portion 201 via the bolts 220.

As further illustrated in FIGS. 11 and 12, the resistance mechanism 203 may include a hydraulic device 224 that extends between the leg support portion 202 and the foot support portion 201. In various embodiments, for example, the hydraulic device 224 may comprise a hydraulic cylinder 225 that extends between and is connected to each of the contoured plate 204 of the leg support portion 202 (e.g., on a side opposite to the leg support surface 240) and the band 215 of the foot support portion 101. As illustrated in FIGS. 11 and 12, the hydraulic cylinder 225 may, for example, be connected to each of the contoured plate 204 and band 215 via a flanged connector 235 that is, for example, bolted onto each respective part.

In such a configuration, the hydraulic cylinder 225 may provide a pressurized resistance to the rotational movement of the foot support portion 201 with respect to the leg support portion 202 about the bolts 220. In various embodiments, for example, the hydraulic cylinder 225 may include a pressurized hydraulic fluid (not shown) in which a piston (not shown) is connected to a piston rod (not shown), such that the piston can move back and forth within the cylinder 225. In this manner, as the piston moves back and forth within the cylinder 225, via the up and down movement of the foot support portion 201, a pressure is exerted on a surface area of the piston to resist the movement of the piston and therefore the foot support portion 201.

Thus, similar to the embodiment of FIGS. 1-10, the foot support portion 201 is able to pivot toward and away from the leg support portion 202 and can have a neutral position relative to the pivot axis P, and, during the rotation of the foot support portion 201, the hydraulic cylinder 225 exerts a force on the foot support portion 201 about the pivot axis P opposite to the respective first and second directions of rotation of the foot support portion 201 about the pivot axis P. Furthermore, the amount of pressure exerted by the hydraulic fluid against the movement of the piston can be adjusted (i.e., to provide more or less resistance against the rotation of the foot support portion 201) as will be understood by those of ordinary skill in the art.

FIGS. 14-16 illustrate an exemplary exercise device 300 in accordance with yet another exemplary embodiment of the present disclosure. Exercise device 300, for example, embodies a soft goods version of the exercise device 100 illustrated in FIGS. 1-10, in which the majority of the frame of the device 100 has been replaced by a soft, material sleeve. As shown in FIGS. 14-16, the exercise device 300 includes a leg support portion 302, a foot support portion 301, and a resistance mechanism 303. Similar to the embodiment of FIGS. 1-10, the foot support portion 301 extends from an end of the leg support portion 302 and is associated with or positioned relative to the leg support portion 302 to pivot relative to the leg support portion around a pivot point associated with a user's ankle, which is where the resistance mechanism 303 is located. In various exemplary embodiments, the leg support portion 302 includes a leg cuff 340 that is configured to receive and surround a leg of a user while the user is using the device 300, and the foot support portion 301 includes a foot cuff 350 that is configured to receive and surround a foot of the user while the user is using the device 300. In order to easily receive the leg and foot of the user, as illustrated in FIG. 16, the device 300 may be placed in an open configuration, in which each of the leg cuff 340 and the foot cuff 350 is unwrapped and loose. In other words, the device 300 may function as a sleeve that opens wide in the front to receive and envelop the foot and leg of the user. Such a configuration may, for example, be particularly useful for non-ambulatory users, users who have a fragile tissue condition (e.g., a surgical site, point of trauma, or general frailty as found in the elderly and chemotherapy patients), and other users who wish to use the device in a supine position, as the open sleeve may allow a user to easily place their foot in the device 300 when the user is lying in bed, as described further below.

The leg support portion 302 includes the leg cuff 340 and an internal frame 304 (see FIG. 15) that is sewn within, for example, a soft material of the leg cuff 340 to prevent the frame 304 from coming into contact with the user's skin. In the orientation of FIGS. 14-16, the internal frame 304 includes a pair of bars 306 that extend downwardly from the leg cuff 340 to connect the leg cuff 340 to the resistance mechanism 303. In a similar manner, the foot support portion 301 includes the foot cuff 350 and an internal frame 308 (see FIG. 15) that is sewn within, for example, a soft material of the foot cuff 350. And, in the orientation of FIGS. 14-16, the internal frame 308 includes a pair bars 314 that extend upwardly from the foot cuff 350 to connect the foot cuff 350 to the resistance mechanism 303. In accordance with various exemplary embodiments, the cuffs 340 and 350 may be made of a dual density foam material, such as, for example a compression molded dual density foam, while the frames 304 and 308 are made from a molded plastic material, such as, for example, a molded polypropylene, polyethylene, nylon, or acrylonitrile butadine (ABS) material as described above with reference to the device 100. Those of ordinary skill in the art will understand, however, that the cuffs 340 and 350 and the frames 304 and 308 may be made of various respective foams and plastics, as well as various other materials suitable for the given application. Suitable materials for the leg and foot cuffs 340 and 350 can include, for example, materials that are relatively light, flexible, breathable (i.e., provide adequate ventilation), and promote free movement so as to facilitate the carrying and comfortable use of the device 300, yet durable and able to withstand repetitive use. Such materials may include, for example, materials that are commonly used in the athletic industry for sports equipment, such as, for example, lacrosse and football pads.

Those of ordinary skill in the art will further understand that various additional embodiments of the present disclosure further contemplate an exercise device 300 that does not utilize an internal frame (i.e., that does not utilize frames 304 and 308). In such an embodiment, for example, the leg and foot cuffs 340 and 350 may be made of a material that is stiff enough to transmit loads to/from the resistance mechanism 303, while still having a soft interior for user comfort.

To more comfortably accommodate various users, respective interior surfaces 305 and 307 of the leg cuff 340 and the foot cuff 350 may each include various additional features and/or liner materials. In various exemplary embodiments, for example, the interior surfaces 305 and 307 may each include a soft, form fitting, fabric liner material 370, including, for example, a shape memory polymer, which may form to different users as would be understood by those of ordinary skill in the art. In various additional exemplary embodiments, the interior surfaces 305 and 307 may each include various friction reducing, cushioning, and/or massaging devices such as, for example, ridges 309 (see FIG. 14). Those ordinarily skilled in the art will understand that the leg cuff 340 and the foot cuff 350 may have various sizes, shapes, configurations and/or features without departing from the scope of the present disclosure. As discussed above and illustrated in FIG. 16, various embodiments of the present disclosure additionally contemplate, for example, incorporating one or more aspects of a variety of medical and/or physical therapy devices within the device 300, such as, for example, within the soft material 370 of the leg cuff 340 and/or foot cuff 350. In accordance with one embodiment, as described above, a temperature regulation device 372, such as for example, a thermoelectric cooler and/or a heater (e.g., chemo-generated or via a battery pack) may be incorporated within the material 370 of one or both of the leg cuff 340 and the foot cuff 350. In accordance with another exemplary embodiment, as described above, the air pockets of a SCD device 374 may be incorporated within the material 370 of the leg cuff 340 (e.g., pouches configured to inflate and deflate with air may be incorporated within the leg cuff 340) in order to facilitate movement of blood within the leg when the user/wearer is inactive. In a further embodiment, as described above, a range of motion assist mechanism 376, such as, for example, an electric motor (which is configured to assist with the rotational movement of the foot cuff 350) may be incorporated within and/or attached to one or both of the internal frames 304 and 308 and/or the material 370 of one or both of the leg cuff 340 and foot cuff 350. Additionally or alternatively, one or both of the leg cuff 340 and the foot cuff 350 may include an electrical stimulation device 378, such as, for example, electrodes configured to stimulate muscles of the leg and/or foot of the user when the device 300 is worn and/or sensors to identify and/or track muscle movement of the user when the device 300 is worn.

As illustrated in FIGS. 14-16, in various exemplary embodiments, each of the leg support portion 302 and the foot support portion 301 may further comprise at least one strap 311. The straps 311 may, for example, be configured to releasably secure around the leg and foot of the user to assist in securing the device 300 to the user. In various embodiments, to prevent user discomfort, the straps 311 may be relatively thick, such that the straps are configured to spread a force load from the device 300 over a relatively large portion of the user's leg and foot. By way of example only, in various embodiments, the straps 311 may comprise hook and loop fasteners, such as, for example, Velcro®. In various embodiments, for example, an interior surface of the straps 311 may include the "hook" portion of the fasteners, and respective outer surfaces of the cuffs 340 and 350 may include a material that acts as the "loop" portion of the fasteners. In this manner, as illustrated in FIG. 16, to receive a leg and foot of a user, the device 300 may be opened by pulling the straps 311 away from the cuffs 340 and 350. And, once the user's leg and foot are within the device 300, the device 300 may be closed and tightened to the appropriate size by again wrapping and securing the straps 311 around and to the cuffs 340 and 350. As above, since the material of the cuffs 340 and 350 itself acts as the "loop" portion of the fasteners to attach to the "hook" portions on the cuffs 311, the cuffs 340 and 350 may be tightened as much as needed to comfortably accommodate the user.

Those ordinarily skilled in the art will understand that the straps 311 may have various configurations, sizes and/or dimensions, as well as various additional features that may help a user to both put on and take off the device 300. In various embodiments, for example, to provide an easy grip for the straps 311, a large plastic tab 312 may be sewn onto a free end of each of the straps 311. Those ordinarily skilled in the art will further understand that the straps 311 may comprise any type and/or configuration of mechanism to releasably secure the leg of the user to the leg cuff 340 and the foot cuff 350, including for example, snaps, buttons, ties, buckles, elastic bands, sliders, and/or any combination thereof.

As above, similar to the embodiment of FIGS. 1-10, the leg support portion 302 is configured to connect to the foot support portion 301 via the resistance mechanism 303 at a pivot axis P. As perhaps best shown in the side view of FIG. 15, the leg cuff 340 is connected to the foot cuff 350 via the resistance mechanism 303, such that a relatively wide opening O is created in the front of the device 300 between the cuffs 340 and 350. The opening O may, for example, be configured to both prevent a user's skin from being pinched between the cuffs 340 and 350 (i.e., while the user is using the device 300) and to increase the range of motion allotted by the device 300.

As shown in FIGS. 14 and 15, one of the bars 306 and one of the bars 314 extends outwardly from the friction device 303 to connect the leg cuff 340 to the foot cuff 350. In other words, the bars 306 and 314 function as arms of the resistance mechanism 303 to both support the respective cuffs 340 and 350 and connect the cuffs 340 and 350 via the pivot P. As illustrated above, with respect to the embodiment of FIGS. 1-10, in various exemplary embodiments, each bar 306 of the leg support portion 302 is configured to mate with a respective bar 314 of the foot support portion 301 to form a hub 320 at which the device 300 pivots. In accordance with one aspect of the present disclosure, each bar 306 may terminate in a housing (see FIG. 7) that is configured to encompass a respective hub 320. In such a configuration, a resistance mechanism 303 may be seated, for example, within one or both of the housings to engage the respective hubs 320. As above, various additional embodiments contemplate a device in which the cuffs 340 and 350 directly connect with the resistance mechanism 303 (i.e., which do not utilize bars 306 and 314). In such an embodiment, in a similar manner, the lines of connection between the cuffs 340 and 350 may meet at the hubs 320. As will be understood by those or ordinary skill in the art, when the device 300 is positioned on a leg of user, the hubs 320 and bars 306 and 314 (or if the bars 306 and 314 are not present, lines of connection) reside along the medial and lateral surfaces of the leg, foot, and ankle of the user.

As shown in FIGS. 14-16, in various exemplary embodiments, to protect the user's ankles, the respective hubs 320 (i.e., on each side of the device 300) and the hardware associated with the resistance mechanism 303 (i.e., that is seated within one of the hubs 320) are each embedded within a soft compression molded casing 330 and padded. As will be understood by those of ordinary skill in the art, the embodiment of FIGS. 14-16 is exemplary only and the resistance mechanism 303 can be integrated within the device 300 using various additional materials and techniques.

In various further embodiments, to provide additional comfort and protection, as further shown in FIGS. 14-16, the casing 330 may form part of a compression molded heel cup 360 that is positioned between the leg cuff 340 and the foot cuff 360 and connected to the cuffs 340 and 350 via an elastic material. In this manner, in conjunction with the leg and foot cuffs 340 and 350, the heel cup 360 is configured to provide a soft, enclosed, boot-like structure to hold the user's leg and foot securely in place. The positioning of the heel cup 360 also serves to provide a relatively continuous surface between the leg and foot cuffs 340 and 350. For example, as the foot cuff 350 rotates with respect to the leg cuff 340 into a position in which the foot is fully extended, the heel cup 360 may slide underneath each of the cuffs 340 and 350. Such a configuration may therefore (1) provide a smooth surface to rotate and slide against the bed/floor when the user is using the device 300 (i.e., flexing their foot), (2) prevent the pinching of sheet fabric between the cuffs when the device 300 is, for example, used in bed, and (3) provide ventilation to the device 300.

Those ordinarily skilled in the art will understand that the leg and foot cuffs 340 and 350 may have various configurations and may be connected to one another using various techniques and mechanisms. Various embodiments of the present disclosure further contemplate, for example, that the leg and foot cuffs 340 and 350 may be disconnected from one another for storage, transport and positioning on a user, and are only connected to each other when the device is being used. Those ordinarily skilled in the art will further understand that the heel cup 360 may have various configurations, sizes, and shapes, and may be formed from various materials, without departing from the scope of the present disclosure. Those ordinarily skill in the art will further understand that the device 300 illustrated in the embodiment of FIGS. 14-16 is exemplary only and that the present disclosure contemplates embodiments that do not utilize a heel cup at all.

As further illustrated above, with respect to the embodiment of FIGS. 1-10, in various exemplary embodiments, the resistance mechanism 303 may comprise a friction device 144 (see FIG. 7) configured to provide a frictional resistance to the rotational movement of the foot support portion 301 about the hubs. Thus, similar to the embodiment of FIGS. 1-10, the foot support portion 301 is able to pivot toward and away from the leg support portion 302 and can have a neutral position relative to the pivot axis P, and, during the rotation of the foot support portion 301, the resistance mechanism 303 exerts a force on the foot support portion 301 about the pivot axis P opposite to the respective first and second directions of rotation of the foot support portion 301 about the pivot axis P. Furthermore, the amount of resistance exerted by the resistance mechanism against the movement of the foot support portion 301 can be adjusted (i.e., to provide more or less resistance against the rotation of the foot support portion 301), via a dial 335, as will be understood by those of ordinary skill in the art.

Figure 22:
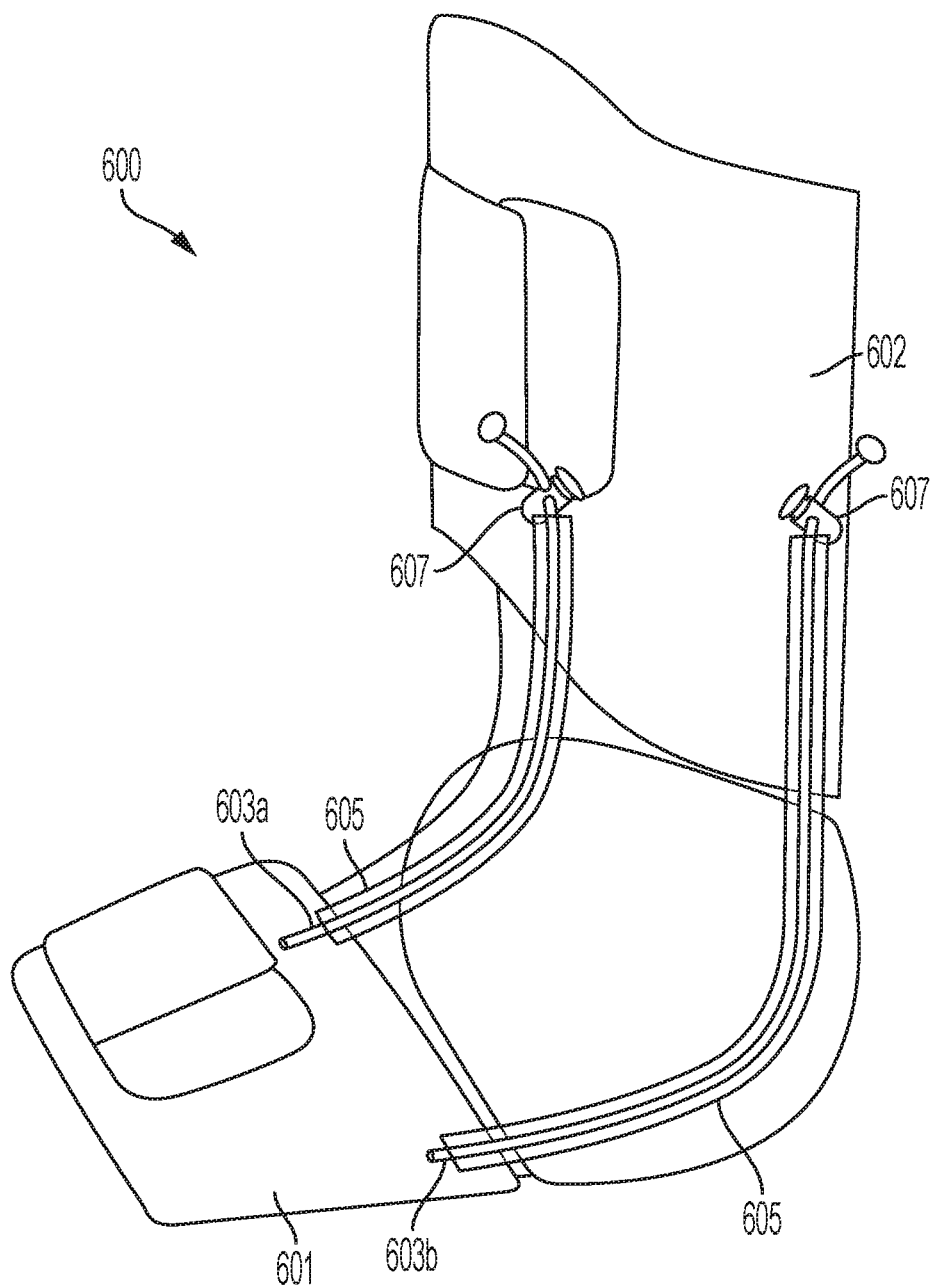
FIG. 22 is a left side view of another exemplary embodiment of an exercise device in accordance with the present disclosure.

As above, those of ordinary skill in the art will understand that the embodiment of FIGS. 14-16 is exemplary only and that various types and/or configurations of resistance mechanisms can be incorporated into the material of the soft goods version of the device (e.g., within the material of the device 300 illustrated in FIGS. 14-16), without departing from the scope of the present disclosure and claims. As illustrated in the embodiment of FIG. 22, for example, one additional exemplary embodiment contemplates an exercise device 600 including a pair of elastic cords (e.g., bungee cords) 603a and 603b that are integrated within the material of the device 600. The elastic cords 603a and 603b may, for example, each be encased within a respective tube (e.g., a polyethylene tube) 605 that is embedded within the material of the device 600. In this manner, the tubes 605 may prevent friction between the cords 603a, 603b and the material of the device 600, and allow free movement of the cords 603a and 603b (i.e., within the device 600) as a foot support portion 601 pivots with respect to a leg support portion 602.

In accordance with various embodiments, for example, the cord 603a that is integrated into a top portion of the device 600 may provide resistance as the foot support portion 601 pivots away from the leg support portion 602 (i.e., during plantar flexion), while the cord 603b that is integrated into a bottom portion of the device 600 may provide resistance as the foot support portion 601 pivots toward the leg support portion 602 (i.e., during dorsiflexion). Furthermore, in such embodiments, the amount of resistance exerted by the cords 603a and 603b against the movement of the foot support portion 601 can be adjusted (i.e., to provide more or less resistance against the rotation of the foot support portion 601), via respective cord locks 607, as will be understood by those of ordinary skill in the art.

In accordance with various exemplary embodiments of the present disclosure, an exemplary method for exercising muscles in an ankle, foot, and/or leg of a user 123 using the exercise device as illustrated in FIGS. 1-10 will now be described with reference to FIGS. 8-10. For use in a sitting position, for example, the exercise device 100 may be placed in a first position, as shown in FIG. 9. Alternatively, for use in a supine position, the exercise device 100 may be placed in a second position, as shown in FIG. 10.

When used in either the sitting or supine position, a leg of the user 123, for example, a left leg 122 is received and supported against the leg support surface 140 of the contoured plate 104 of the leg support portion 102, and a foot 121 of the user 123, for example, a left foot 121 is set on the foot support surface 150 of the foot support portion 101. In various embodiments, for example, the leg 122 is positioned within the contoured plate 104 and against the leg support surface 140 of the leg support portion 102 such that the leg support portion 102 at least partially wraps around a shin 124 of the leg 122. The leg 122 is releasably secured to the leg support portion 102 by securing the strap 111 around the shin 124 and the foot 121 is releasably secured to the foot support portion 101 by securing the respective straps 116 around the foot 121. As shown in FIGS. 9 and 10, for example, various exemplary embodiments contemplate securing the left leg 122 and left foot 121 respectively to the leg support portion 102 and the foot support portion 101 with the respective straps 111 and 116. As above, by way of example only, various embodiments contemplate securing the left leg 122 and the left foot 121 respectively to the leg support portion 102 and the foot support portion 101 with hook and loop fasteners, such as, for example, Velcro®.

As also shown in FIGS. 9 and 10, upon initial use of the exercise device 100, the foot support portion 101 may receive the user's 123 foot 121 in the neutral position relative to a pivot axis P. As shown for illustrative purposes in FIGS. 8A and 8B, using for example a left foot 121, the user 123 can rotate the foot support portion 101 in first and second opposite directions A and B about the pivot axis P (i.e., away from and toward the leg support portion 102) against a force F exerted against the foot support portion 101 in a direction opposite to the rotating direction (i.e., opposite to the direction A or B). Thus, in various exemplary embodiments, as illustrated in FIG. 8A, rotating the foot support portion 101 in the first direction A comprises moving the foot support portion 101 away from the leg support portion 102 (i.e., depressing the foot support portion 101) and, as shown in FIG. 8B, rotating the foot support portion 101 in the second direction B comprises moving the foot support portion 101 toward the leg support portion 102 (i.e., raising the foot support portion 101).

As explained above, in various exemplary embodiments, the amount of force exerted against the foot support portion 101 is constant throughout all movements of the foot support portion 101 (i.e., the force exerted against the rotation of the foot support portion 101 as it moves away from the neutral position in the first direction A is the same as the force exerted against the rotation of the foot support portion 101 as it moves back to the neutral position in the second direction B.) In this manner, the foot support portion 101 may be rotated against a constant, passive resistance force throughout a full range of ankle flexion and extension of the foot 121. While, in various additional exemplary embodiments, the amount of force exerted against the foot support portion 101 (e.g., in the form of a stored torque) may vary with a degree of rotation θ of the foot support portion 101 about the pivot axis P, for example, the amount of torque exerted against the foot support portion 101 may increase with the degree of rotation θ of the foot support portion 101 about the pivot axis P. In this way, the further away from the neutral position the user 123 rotates the foot support portion 101, the more force that is required by the user 123 to maintain the position of the foot support portion 101.

As above, to aid with compliance monitoring and goal tracking, various exemplary embodiments of the present disclosure also contemplate using a compliance monitoring device, such as, for example, a tally counter type compliance monitoring device 160 to count and show on a display 161 a number of repetitions made by the foot support portion 101.

Although not shown, similarly, the device may be used with a right leg 132/right foot 131 of the user 123 (see FIGS. 9 and 10). For example, in the same manner, the right leg 132 may be received and supported against the leg support surface 140 of the contoured plate 104 of the leg support portion 102, and the foot 131 may be set on the foot support surface 150 of the foot support portion 101. As above, the user 123 can then rotate the foot support portion 101 in first and second opposite directions A and B about the pivot axis P (i.e., away from and toward the leg support portion 102)

against a force exerted against the foot support portion 101 in a direction opposite to the rotating direction (i.e., opposite to the direction A or B).

Various exemplary embodiments of the present disclosure, therefore, contemplate rotating the foot support portion 101 in the first and/or second opposite directions A and B to subject the corresponding foot 121 or 131 of a user to both plantar flexion motion (e.g., with reference to FIG. 8A., movement of the toes 133 of the left foot 121 away from the left shin 124, thereby contracting the left calf muscle 145) and dorsiflexion motion (e.g., with reference to FIG. 8B, movement of the toes 133 of the left foot 121 toward the left shin 124, thereby stretching the left calf muscle 145) respectively. In this manner, using the exercise devices in accordance with various exemplary embodiments of the present disclosure can exercise both dorsiflexor and plantar flexor muscle groups, thereby providing a full range of ankle flexion and extension for a user.

In various exemplary embodiments of the present disclosure, for example, rotation of the foot support portion 101 in the direction A may subject the corresponding foot through up to about 75 degrees of plantar flexion (e.g., rotation ranging from about neutral to 75 degrees, or 90 degrees to about 165 degrees from the leg support portion 102); and rotation of the foot support portion 101 in the direction B may subject the corresponding foot through up to about 60 degrees of dorsiflexion (e.g., rotation ranging from about neutral to −60 degrees, or 90 degrees to about 30 degrees from the leg support portion 102).

Thus, as above, in various exemplary embodiments, the resistance mechanism 103 is configured to exert a force on the foot support portion 101 when the foot support portion 101 is rotated away from the neutral position (as shown in FIGS. 8A and 8B, wherein the neutral position is represented by the dotted lines), thereby providing for a full range of ankle flexion and extension for the user 123 using the exercise device 100. In various exemplary embodiments, the device 100 is, therefore, configured to exercise muscles in each ankle, foot, and/or leg of the user 123 to increase blood circulation. Those of ordinary skill in the art would understand that the resistance mechanism may have various configurations, and may exert various types and amounts of force to counteract the movement of the foot support portion 101. In various exemplary embodiments, for example, a user may adjust the amount of counteracting force exerted by the resistance mechanism 103 against the foot support portion 101 to increase and/or decrease the amount of effort required to move the foot support portion. Accordingly, one of ordinary skill in the art would understand that the counteracting force is a resistance that can vary based on the type of resistance mechanism used, and that the resistance of the resistance mechanism can be selected based on the person that is using the device 100. One of ordinary skill in the art would know how to select a resistance mechanism for the device based on the counteracting force required for a selected application.

In general, the resistance provided by various exemplary devices in accordance with the present disclosure can be selected and the devices modified accordingly based on such factors as the age of a person for whom the device is intended, the relative strength or weakness of a person for whom the device is intended, the level of exercise desired, and other such factors that those of ordinary skill in the art would appreciate.

Figure 21:
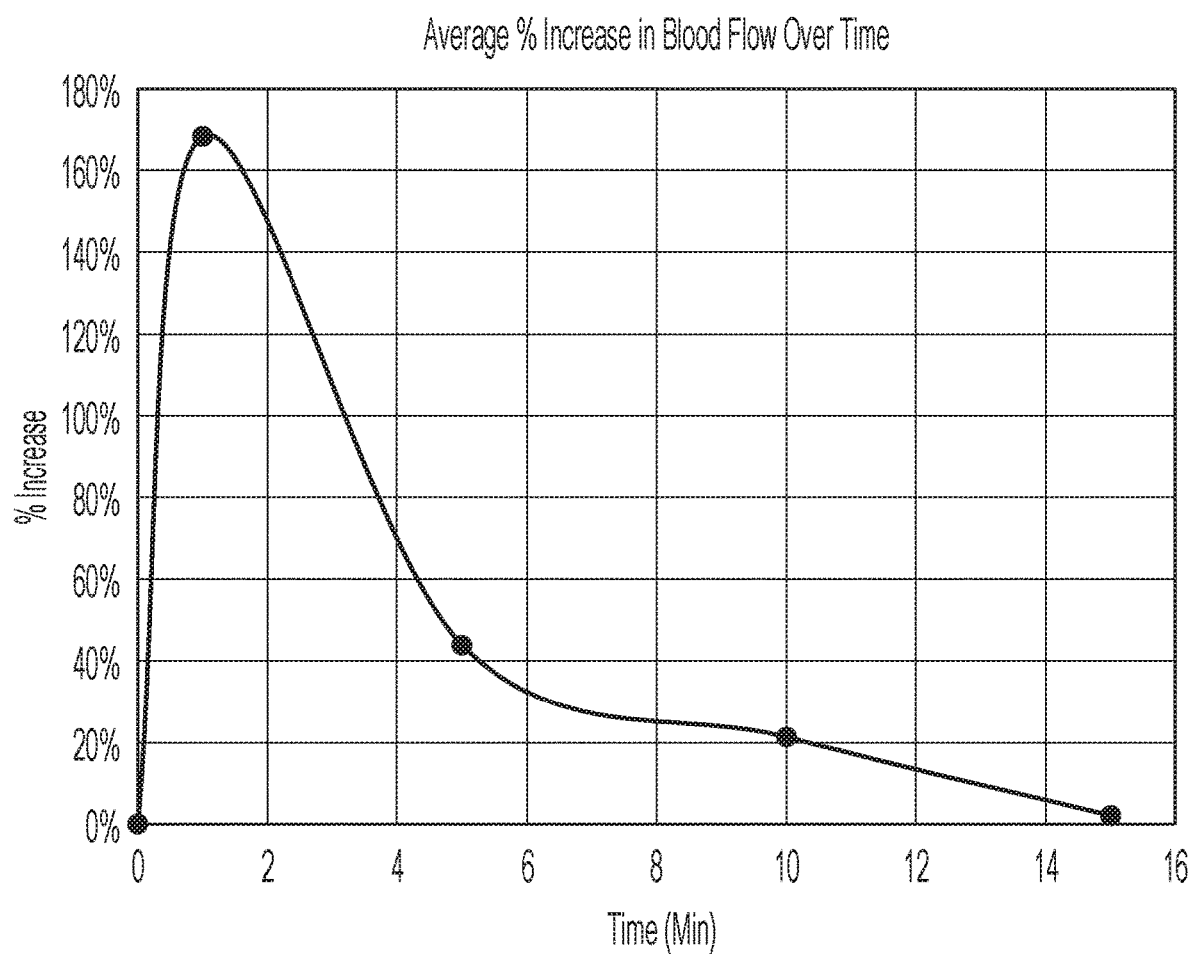
FIG. 21 is a graph illustrating the average percentage increase in blood flow over time during use of an exercise device in accordance with the present disclosure.

To demonstrate the efficacy of the devices, a clinical pilot study was performed using 12 healthy, adult volunteers. In the study, each participant used a similar device to the above device 100 to exercise, while being monitored by ultrasound Doppler using a linear probe. The subjects were each supine with straight legs (as close to 0 degrees of flexion as possible), with one foot engaged with an exercise device. Each subject rested in the supine position until blood flow parameters stabilized, after which time resting blood flow measurements were conducted. Blood vessel diameter measurements were taken using the ultrasound Doppler as visualized on the screen and the diameter was observed to remain constant before and through the exercise. Each participant then commenced with 1 minute of exercise, performing maximum effort lower limb plantar/dorsiflexion maneuvers at a rate of 30 cycles per minute as indicated by a metronome (i.e., wherein one cycle was defined as going from maximum dorsiflexion to maximum plantar flexion and back to the starting position). Blood flow measurements were then repeated immediately following completion of exercise, and then at 5 minutes, 10 minutes, and 15 minutes following completion of exercise. Post-exercise values for blood flow velocity and blood vessel diameter were then divided by pre-exercise values to calculate the respective ratios of each. The results of the clinical study are illustrated in FIG. 21, which plots the average percentage increase in blood flow over time for the participants. As shown in FIG. 21, on average, the participants experienced a significant improvement in blood flow velocity through the popliteal vein immediately after use, with the average increase in blood flow velocity at 1 minute being about 168%. The duration of continued increase in blood flow velocity relative to starting levels varied somewhat, but the average increase in blood flow velocity at 5 minutes was about 44%. Although the study specifically measured blood velocity, one of ordinary skill in the art, understanding the relationship between flow, velocity, and area (diameter of the vein) will understand that it is believed a corresponding increase in the volume of blood moving through the veins was realized.

It will be appreciated by those ordinarily skilled in the art having the benefit of this disclosure that the present disclosure provides various exemplary devices and methods for exercising muscles in an ankle, foot, and/or leg useful for increasing blood circulation in the lower extremities of the body. Furthermore, those ordinarily skilled in the art will understand that the disclosed exemplary devices and methods for exercising muscles in an ankle, foot, and/or leg may have other benefits and may treat other conditions, including, but not limited to, peripheral vascular disease, such as peripheral artery disease, PAD, and chronic venous insufficiency.

Further modifications and alternative embodiments of various aspects of the present disclosure will be apparent to those skilled in the art in view of this description. For example, although the particular examples and embodiments set forth herein contemplate an exercise device that receives one leg/foot at a time, various additional exemplary embodiments in accordance with the present disclosure contemplate an exercise device that receives both legs/feet at once, thereby simultaneously exercising muscles in both ankles, feet and/or legs.

Furthermore, the devices and methods may include additional components or steps that were omitted from the drawings for clarity of illustration and/or operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents.

It is to be understood that the particular examples and embodiments set forth herein are non-limiting, and modifications to structure, dimensions, materials, and methodologies may be made without departing from the scope of the present disclosure.

Furthermore, this description's terminology is not intended to limit the present disclosure. For example, spatially relative terms—such as "beneath", "below", "lower", "above", "upper", "bottom", "right", "left" and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in FIGS. 1-12.

For the purposes of this specification and appended claims, unless otherwise indicated, all numbers expressing quantities, percentages or proportions, and other numerical values used in the specification and claims, are to be understood as being modified in all instances by the term "about" if they are not already. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It should be understood that while the present disclosure has been described in detail with respect to various exemplary embodiments thereof, it should not be considered limited to such, as numerous modifications are possible without departing from the broad scope of the appended claims, including the equivalents they encompass.

We claim:

1. An exercise device comprising:
    a foot support portion comprising a foot support surface configured to support and stimulate a user's foot positioned in the foot support portion, the foot support portion being pivotably connected to a leg support portion via a heel cup and having a neutral position relative to a pivot axis, the foot support portion being configured to rotate about the pivot axis in a first direction away from the neutral position and in a second direction away from the neutral position, wherein the second direction is opposite the first direction, and wherein the foot support portion is configured to rotate about the pivot axis throughout a full range of ankle flexion and extension of the user's foot, the full range of ankle flexion and extension comprising about 75 degrees of plantar flexion motion in the first direction and about 60 degrees of dorsiflexion motion in the second direction; and
    a resistance mechanism configured to exert a force on the foot support portion about the pivot axis opposite to the respective first and second directions of rotation of the foot support portion about the pivot axis,
    wherein each of the foot support portion and the leg support portion comprises a sleeve made of a soft material, each sleeve being configured to respectively receive and enclose the user's foot and a user's leg, and
    wherein the heel cup is positioned between the foot and leg support portions and is configured to slide relative to each of the respective foot and leg support portions during rotation of the foot support portion about the pivot axis.

2. The exercise device of claim 1, wherein the pivot axis is configured to coincide with a natural pivot axis of an ankle of a user of the exercise device.

3. The exercise device of claim 2, wherein the resistance mechanism comprises only one resistance mechanism positioned at the pivot axis on only one side of the exercise device.

4. The exercise device of claim 1, wherein the resistance mechanism comprises at least one of a friction device, a spring device, and a hydraulic device.

5. The exercise device of claim 4, wherein the friction device comprises an assembly of stacked washers, including a tabbed drag washer sandwiched between a pair of keyed drag washers, and a wave spring configured to assist with modulation of a pressure applied to the assembly of stacked washers.

6. The exercise device of claim 1, wherein the force exerted by the resistance mechanism provides a passive resistance to rotational movement of the foot support portion throughout the full range of ankle flexion and extension of the foot.

7. The exercise device of claim 1, wherein an amount of the force exerted by the resistance mechanism is constant throughout an entire range of motion of the foot support portion.

8. The exercise device of claim 1, wherein an amount of the force exerted by the resistance mechanism varies with a degree of rotation of the foot support portion.

9. The exercise device of claim 1, wherein the exercise device is configured to exercise muscles in an ankle, foot, and/or leg of a user to increase blood circulation.

10. The exercise device of claim 1, further comprising a compliance monitoring device, the compliance monitoring device being configured to track a number of repetitions made by the foot support portion.

11. The exercise device of claim 1, wherein one or both of the foot and leg support portions comprises a liner material the liner material comprising one or more of air pockets configured to exert pressure on the user's foot and/or the user's leg, heating elements, electrodes configured to stimulate muscles of the user's foot and/or the user's leg, and/or sensors configured to identify and/or track muscle movement of the user's foot and/or the user's leg.

12. The exercise device of claim 1, wherein the foot support surface is configured to massage the user's foot and/or apply pressure to a sole of the user's foot, during rotation of the foot support portion about the pivot axis.

13. The exercise device of claim 1, wherein the foot support portion, the heel cup, and the leg support portion together form a soft, enclosed, boot-like structure configured to receive the user's foot and leg.

14. The exercise device of claim 1, wherein the heel cup is configured to receive and surround an ankle of the user.

15. The exercise device of claim 14, wherein the resistance mechanism is embedded within the heel cup.

16. The exercise device of claim 15, wherein the heel cup is formed from a compression molded material and the resistance mechanism includes a casing forming part of the compression molded material.

17. The exercise device of claim 1, wherein the resistance mechanism comprises elastic bands integrated within the soft material of the foot and leg support portions.

18. The exercise device of claim 1, wherein the exercise device comprises only one resistance mechanism, the one resistance mechanism being positioned at the pivot axis of the foot support portion on only one side of the foot support portion.

19. The exercise device of claim 1, wherein the heel cup is configured to slide under each of the respective foot and leg support portions during rotation of the foot support portion about the pivot axis.

20. A method for exercising muscles in an ankle, foot, and/or leg of a user, comprising:
with a foot of the user positioned within a foot support portion of an exercise device and a leg of the user positioned within a leg support portion of the exercise device:
rotating the foot support portion relative to the leg support portion in a first direction of rotation about a pivot axis of the exercise device and against a force exerted by a resistance mechanism of the exercise device in a second direction of rotation, opposite to the first direction of rotation;
rotating the foot support portion relative to the leg support portion in the second direction of rotation about the pivot axis and against a force exerted by the resistance mechanism in the first direction of rotation; and
sliding each of the foot and leg support portions relative to a heel cup positioned between the foot and leg support portions during rotation of the foot support portion relative to the leg support portion in the first and second directions of rotation.

21. The method of claim 20, wherein rotating the foot support portion in the first and second directions of rotation comprises rotating the foot support portion about an axis provided by an ankle of the user, and wherein rotating the foot support portion in the first direction of rotation comprises moving the foot support portion away from the leg support portion and rotating the foot support portion in the second direction of rotation comprises moving the foot support portion toward the leg support portion.

22. The method of claim 20, wherein rotating the foot support portion in the first and second directions of rotation comprises rotating the foot support portion against a passive resistance throughout a full range of ankle flexion and extension of the foot, the full range of ankle flexion and extension comprising about 75 degrees of plantar flexion motion in the first direction of rotation and about 60 degrees of dorsiflexion motion in the second direction of rotation.

23. The method of claim 20, wherein rotating the foot support portion in the first and second directions of rotation comprises rotating the foot support portion against a constant force.

24. The method of claim 20, wherein rotating the foot support portion in the first and second directions of rotation increases blood flow velocity through a popliteal vein of the user compared to a resting level of blood flow velocity through the popliteal vein of the user.

25. The method of claim 24, wherein rotating the foot support portion in the first and second directions of rotation increases the blood flow velocity by about 168 percent compared to the resting level of blood flow velocity.

26. The method of claim 20, further comprising supplying one or more of sequential compression, temperature regulation, and electrical stimulation, and/or range of motion assist, to the foot and/or the leg of the user via a liner material of the foot support portion and/or the leg support portion while rotating the foot support portion in the first and second directions of rotation.

27. The method of claim 20, wherein sliding each of the foot and leg support portions relative to the heel cup comprises sliding the heel cup under each of the respective foot and leg support portions.

* * * * *